US011204323B2

(12) United States Patent
Diamond et al.

(10) Patent No.: US 11,204,323 B2
(45) Date of Patent: *Dec. 21, 2021

(54) DEVICE AND ASSOCIATED METHODS FOR PERFORMING LUMINESCENCE AND FLUORESCENCE MEASUREMENTS OF A SAMPLE

(71) Applicant: Hycor Biomedical, LLC, Indianapolis, IN (US)

(72) Inventors: Ronald Norman Diamond, Anaheim Hills, CA (US); Steven Michael Gann, Huntington Beach, CA (US); Eric Darnell Hall, Huntington Beach, CA (US); Tae Ho Hwang, Brea, CA (US); John Lewis Morton, Canyon Lake, CA (US); Anatoly Moskalev, Irvine, CA (US); Bruce Alan Sargeant, Orange, CA (US); Dennis Edwin Rieger, Hermosa Beach, CA (US); Marinela Gombosev, Newport Beach, CA (US); Mark David Van Cleve, Long Beach, CA (US)

(73) Assignee: Hycor Biomedical, LLC, Indianapolis, IN (US)

( * ) Notice: Subject to any disclaimer, the term of this patent is extended or adjusted under 35 U.S.C. 154(b) by 77 days.

This patent is subject to a terminal disclaimer.

(21) Appl. No.: 15/681,647

(22) Filed: Aug. 21, 2017

(65) Prior Publication Data

US 2017/0370928 A1    Dec. 28, 2017

Related U.S. Application Data

(63) Continuation of application No. 14/634,011, filed on Feb. 27, 2015, now Pat. No. 9,753,033, which is a
(Continued)

(51) Int. Cl.
*G01N 33/564* (2006.01)
*G01N 21/64* (2006.01)
(Continued)

(52) U.S. Cl.
CPC ....... *G01N 21/645* (2013.01); *G01N 21/6428* (2013.01); *G01N 21/76* (2013.01);
(Continued)

(58) Field of Classification Search
CPC .. G01N 21/645; G01N 21/76; G01N 21/6428; G01N 2021/6484;
(Continued)

(56) References Cited

U.S. PATENT DOCUMENTS 3,628,682 A    12/1971   Paulson
3,729,556 A     4/1973   Schwarz
(Continued)

FOREIGN PATENT DOCUMENTS

CN    101696973 A    4/2010
CN    102478571 A    5/2012
(Continued)

OTHER PUBLICATIONS

International Application No. PCT/US2015/023408 filed on Mar. 30, 2015.
(Continued)

*Primary Examiner* — Christopher Adam Hixson
(74) *Attorney, Agent, or Firm* — K&L Gates LLP; Louis C. Cullman; Dennis A. Majewski

(57) ABSTRACT

Apparatuses and methods of optically analyzing fluid within a pipette are described herein. In an embodiment, an optical reader subassembly includes a pipette configured to aspirate and hold a fluid sample within its tip, a housing configured to receive at least the tip of the pipette through a reentrant seal so that the tip of the pipette is located in a light tight
(Continued)

manner within an internal area, a light source positioned to be in proximity to the tip of the pipette when the tip of the pipette is received by the housing, the light source configured to project light through the tip of the pipette and onto the fluid sample held within the tip, and an optical sensor configured to take a reading of the fluid sample held within the tip of the pipette without any of the fluid sample being injected from the pipette.

18 Claims, 13 Drawing Sheets

Related U.S. Application Data continuation of application No. 14/215,861, filed on Mar. 17, 2014, now Pat. No. 9,075,055.

(60) Provisional application No. 61/791,295, filed on Mar. 15, 2013, provisional application No. 61/791,879, filed on Mar. 15, 2013.

(51) Int. Cl.
| | |
|---|---|
| *G01N 21/76* | (2006.01) |
| *G01N 33/53* | (2006.01) |
| *G01N 33/543* | (2006.01) |
| *G01N 33/569* | (2006.01) |
| *G01N 33/58* | (2006.01) |
| *G01N 33/68* | (2006.01) |
| *G01N 35/00* | (2006.01) |
| *G01N 35/10* | (2006.01) |
| *G01N 35/04* | (2006.01) |

(52) U.S. Cl.
CPC ..... *G01N 33/5306* (2013.01); *G01N 33/5434* (2013.01); *G01N 33/54326* (2013.01); *G01N 33/54393* (2013.01); *G01N 33/564* (2013.01); *G01N 33/569* (2013.01); *G01N 33/5695* (2013.01); *G01N 33/56983* (2013.01); *G01N 33/582* (2013.01); *G01N 33/6854* (2013.01); *G01N 33/6893* (2013.01); *G01N 35/0098* (2013.01); *G01N 35/1011* (2013.01); *G01N 2021/6484* (2013.01); *G01N 2035/0453* (2013.01); *G01N 2035/1062* (2013.01); *G01N 2201/062* (2013.01); *G01N 2201/08* (2013.01); *G01N 2333/4703* (2013.01); *G01N 2333/62* (2013.01); *G01N 2333/78* (2013.01); *G01N 2800/24* (2013.01); *Y10T 436/119163* (2015.01)

(58) Field of Classification Search
CPC ......... G01N 2201/08; G01N 2201/062; G01N 33/54393; G01N 33/564; G01N 33/6854; G01N 33/5306; G01N 33/54326; G01N 33/582; G01N 33/6893; G01N 33/569; G01N 35/1011; G01N 35/0098; G01N 2035/1062; G01N 2035/0453; G01N 2333/62; G01N 2333/4703; G01N 2333/78; Y10T 436/119163
See application file for complete search history.

(56) References Cited

U.S. PATENT DOCUMENTS

| | | | |
|---|---|---|---|
| 4,291,230 A | 9/1981 | Heiss | |
| 4,778,751 A | 10/1988 | El Shami et al. | |
| 4,849,337 A | 7/1989 | Calenoff et al. | |
| 5,001,049 A | 3/1991 | Klein et al. | |
| 5,395,752 A | 3/1995 | Law et al. | |
| 5,395,938 A | 3/1995 | Ramakrishnan | |
| 5,468,453 A | 11/1995 | Holt | |
| 5,543,332 A | 8/1996 | Lihme et al. | |
| 5,583,001 A | 12/1996 | Bobrow et al. | |
| 5,643,566 A | 7/1997 | Hanisch et al. | |
| 5,672,475 A | 9/1997 | Lee et al. | |
| 5,674,698 A | 10/1997 | Zarling et al. | |
| 5,686,253 A | 11/1997 | Skold et al. | |
| 5,690,907 A | 11/1997 | Lanza et al. | |
| 5,698,397 A | 12/1997 | Zarling et al. | |
| 5,736,353 A | 4/1998 | Weavers et al. | |
| 5,770,700 A | 6/1998 | Webb et al. | |
| 5,776,487 A | 7/1998 | Wilson et al. | |
| 5,776,785 A | 7/1998 | Lin et al. | |
| 5,804,391 A | 9/1998 | Klemt et al. | |
| 5,807,997 A | 9/1998 | Batista | |
| 5,879,885 A | 3/1999 | Becker | |
| 5,879,888 A | 3/1999 | Aizawa et al. | |
| 5,922,558 A | 7/1999 | Akhavan-Tafti | |
| 5,942,407 A | 8/1999 | Liotta et al. | |
| 5,952,238 A | 9/1999 | Tsuji et al. | |
| 5,965,378 A | 10/1999 | Schlieper et al. | |
| 5,973,124 A | 10/1999 | Bayer et al. | |
| 5,994,519 A | 11/1999 | Osbourn et al. | |
| 6,059,561 A | 5/2000 | Becker | |
| 6,066,448 A | 5/2000 | Wohlstadter et al. | |
| 6,066,462 A | 5/2000 | Goueli | |
| 6,068,979 A | 5/2000 | Akhavan-Tafti | |
| 6,087,188 A | 7/2000 | Johansen et al. | |
| 6,090,545 A | 7/2000 | Wohlstadter et al. | |
| 6,103,537 A | 8/2000 | Ullman et al. | |
| 6,140,045 A | 10/2000 | Wohlstadter et al. | |
| 6,153,442 A | 11/2000 | Pirio et al. | |
| 6,159,699 A | 12/2000 | Brown et al. | |
| 6,165,800 A | 12/2000 | Jiang et al. | |
| 6,180,336 B1 | 1/2001 | Osbourn et al. | |
| 6,180,340 B1 | 1/2001 | Nelson | |
| 6,235,480 B1 | 5/2001 | Shultz et al. | |
| 6,303,325 B1 | 10/2001 | Mehta et al. | |
| 6,328,934 B1 | 12/2001 | Ljung et al. | |
| 6,342,588 B1 | 1/2002 | Osbourn et al. | |
| 6,348,310 B1 | 2/2002 | Goueli | |
| 6,350,579 B1 | 2/2002 | Nelson | |
| 6,379,909 B1 | 4/2002 | Ipsen et al. | |
| 6,399,299 B1 | 6/2002 | Bobrow et al. | |
| 6,399,397 B1 | 6/2002 | Zarling et al. | |
| 6,432,662 B1 | 8/2002 | Davis et al. | |
| 6,489,123 B2 | 12/2002 | Osbourn et al. | |
| 6,489,309 B1 | 12/2002 | Singh et al. | |
| 6,528,322 B1 | 3/2003 | Carlsson et al. | |
| 6,537,829 B1 | 3/2003 | Zarling et al. | |
| 6,730,479 B2 | 5/2004 | Shultz et al. | |
| 6,733,980 B1 | 5/2004 | Venge et al. | |
| 6,737,278 B1 | 5/2004 | Carlsson et al. | |
| 6,753,157 B2 | 6/2004 | Goueli | |
| 6,777,198 B2 | 8/2004 | Mendel-Hartvig et al. | |
| 6,806,058 B2 | 10/2004 | Jesperson et al. | |
| 6,812,038 B1 | 11/2004 | Mendel-Hartvig et al. | |
| 6,872,828 B2 | 3/2005 | Akhavan-Tafti et al. | |
| 6,897,036 B2 | 5/2005 | Akhavan-Tafti et al. | |
| 6,902,889 B1 | 6/2005 | Carlsson et al. | |
| 6,924,154 B2 | 8/2005 | Evangelista et al. | |
| 6,939,681 B1 | 9/2005 | Ipsen et al. | |
| 6,949,524 B2 | 9/2005 | Singh et al. | |
| 6,958,214 B2 | 10/2005 | Braun | |
| 6,972,326 B2 | 12/2005 | Haugland et al. | |
| RE39,047 E | 3/2006 | Aizawa et al. | |
| 7,018,847 B2 | 3/2006 | Mendel-Hartvig et al. | |
| 7,074,622 B2 | 7/2006 | Qiao et al. | |
| 7,083,986 B2 | 8/2006 | Natrajan et al. | |
| 7,097,995 B2 | 8/2006 | Jiang et al. | |
| 7,102,005 B2 | 9/2006 | Agnew et al. | |
| 7,183,072 B1 | 2/2007 | Hainfeld | |
| 7,183,119 B2 | 2/2007 | Qiao et al. | |
| 7,247,726 B2 | 7/2007 | Akhavan-Tafti et al. | |
| 7,262,019 B2 | 8/2007 | Kovalenko | |
| 7,297,555 B2 | 11/2007 | Evangelista et al. | |
| 7,300,655 B2 | 11/2007 | Hansen et al. | |
| 7,309,615 B2 | 12/2007 | Natrajan et al. | |

(56) References Cited

U.S. PATENT DOCUMENTS

| | | |
|---|---|---|
| 7,319,041 B2 | 1/2008 | Natrajan et al. |
| 7,364,872 B1 | 4/2008 | Hainfeld |
| 7,381,797 B2 | 6/2008 | Woerner et al. |
| 7,393,638 B2 | 7/2008 | Chou |
| 7,405,084 B1 | 7/2008 | Mendel-Hartvig et al. |
| 7,439,014 B2 | 10/2008 | Pamula et al. |
| 7,445,894 B2 | 11/2008 | Agnew et al. |
| 7,459,284 B2 | 12/2008 | Jiang et al. |
| 7,491,553 B2 | 2/2009 | Brown et al. |
| 7,501,498 B2 | 3/2009 | Hansen et al. |
| 7,514,223 B2 | 4/2009 | Yang et al. |
| 7,521,184 B2 | 4/2009 | Radka et al. |
| 7,521,577 B2 | 4/2009 | Gee et al. |
| 7,556,928 B2 | 7/2009 | Jesperson et al. |
| 7,560,556 B2 | 7/2009 | Akhavan-Tafti et al. |
| 7,563,566 B2 | 7/2009 | Woerner et al. |
| 7,592,153 B2 | 9/2009 | Hainfeld |
| 7,611,909 B1 | 11/2009 | Natrajan et al. |
| 7,674,629 B2 | 3/2010 | Waheed et al. |
| 7,759,133 B2 | 7/2010 | Van Neerven |
| 7,785,904 B2 | 8/2010 | Natrajan et al. |
| 7,799,534 B2 | 9/2010 | Akhavan-Tafti |
| 7,824,928 B2 | 11/2010 | Evangelista et al. |
| 7,833,983 B2 | 11/2010 | Mahler |
| 7,842,475 B2 | 11/2010 | Zheng et al. |
| 7,842,784 B2 | 11/2010 | Nakayama et al. |
| 7,851,184 B2 | 12/2010 | Pollack et al. |
| 7,871,781 B2 | 1/2011 | Rundstrom et al. |
| 7,875,467 B2 | 1/2011 | Natrajan et al. |
| 7,879,575 B2 | 2/2011 | Kricka et al. |
| 7,888,060 B2 | 2/2011 | Hainfeld et al. |
| 7,892,853 B2 | 2/2011 | Brown et al. |
| 7,906,293 B2 | 3/2011 | Mattingly et al. |
| 7,923,214 B2 | 4/2011 | Akhavan-Tafti |
| 7,951,554 B2 | 5/2011 | Hainfeld et al. |
| 7,951,910 B2 | 5/2011 | Schwarz et al. |
| 7,985,557 B2 | 7/2011 | Kosmeder et al. |
| 8,034,631 B2 | 10/2011 | Brown et al. |
| 8,034,632 B2 | 10/2011 | Brown et al. |
| 8,093,066 B2 | 1/2012 | Brown et al. |
| 8,342,736 B2 | 1/2013 | Luotola et al. |
| 8,349,620 B2 | 1/2013 | Brown et al. |
| 9,075,055 B2 | 7/2015 | Diamond et al. |
| 9,651,550 B2 | 5/2017 | Van Cleve et al. |
| 9,658,225 B2 | 5/2017 | Van Cleve et al. |
| 9,658,226 B2 | 5/2017 | Van Cleve et al. |
| 9,753,033 B2 | 9/2017 | Diamond et al. |
| 9,766,233 B2 | 9/2017 | Diamond et al. |
| 2003/0031685 A1 | 2/2003 | Stumvoll et al. |
| 2003/0042428 A1 | 3/2003 | Peukert et al. |
| 2003/0073121 A1 | 4/2003 | Mendel Hartvig et al. |
| 2004/0023309 A1 | 2/2004 | Noll |
| 2004/0023412 A1 | 2/2004 | Carlsson et al. |
| 2004/0118941 A1* | 6/2004 | Joseph ............... B05B 7/2478 239/302 |
| 2004/0202577 A1 | 10/2004 | McNeil et al. |
| 2004/0222384 A1 | 11/2004 | Lee et al. |
| 2005/0244828 A1 | 11/2005 | Kreitman et al. |
| 2006/0008895 A1 | 1/2006 | Chen et al. |
| 2006/0127281 A1 | 6/2006 | Bjorson et al. |
| 2006/0252097 A1 | 11/2006 | Deutscher et al. |
| 2007/0161055 A1 | 7/2007 | Corry et al. |
| 2007/0166776 A1 | 7/2007 | Noll |
| 2007/0183978 A1 | 8/2007 | Preuss et al. |
| 2007/0254308 A1 | 11/2007 | Bobrow et al. |
| 2007/0282362 A1 | 12/2007 | Berg et al. |
| 2008/0003142 A1 | 1/2008 | Link et al. |
| 2008/0124738 A1 | 5/2008 | Green et al. |
| 2008/0293161 A1 | 11/2008 | Deutscher et al. |
| 2009/0088336 A1 | 4/2009 | Burd et al. |
| 2009/0176201 A1 | 7/2009 | Jablonski et al. |
| 2009/0286258 A1 | 11/2009 | Kaur et al. |
| 2009/0298199 A1 | 12/2009 | Corry et al. |
| 2010/0075374 A1 | 3/2010 | Lim et al. |
| 2010/0190689 A1 | 7/2010 | Thornton et al. |
| 2010/0284583 A1 | 11/2010 | Ljung |
| 2010/0332143 A1 | 12/2010 | Onell et al. |
| 2011/0076692 A1 | 3/2011 | Sista et al. |
| 2011/0151582 A1 | 6/2011 | Basile |
| 2011/0275095 A1 | 11/2011 | Babson |
| 2011/0287455 A1 | 11/2011 | Venge |
| 2012/0077286 A1 | 3/2012 | Brown et al. |
| 2012/0264230 A1 | 10/2012 | Brown et al. |
| 2014/0274784 A1 | 9/2014 | Van Cleve et al. |
| 2015/0177145 A1 | 6/2015 | Diamond et al. |
| 2015/0177146 A1 | 6/2015 | Diamond et al. |
| 2015/0204867 A1 | 7/2015 | Van Cleve et al. |
| 2015/0204871 A1 | 7/2015 | Van Cleve et al. |
| 2017/0205410 A1 | 7/2017 | Van Cleve et al. |
| 2017/0212110 A1 | 7/2017 | Van Cleve et al. |
| 2017/0212111 A1 | 7/2017 | Van Cleve et al. |
| 2017/0370841 A1 | 12/2017 | Diamond et al. |

FOREIGN PATENT DOCUMENTS

| | | |
|---|---|---|
| EP | 0353592 A2 | 2/1990 |
| EP | 0355849 A2 | 2/1990 |
| EP | 0981043 A1 | 2/2000 |
| EP | 1054250 A1 | 11/2000 |
| EP | 1279946 A2 | 1/2003 |
| EP | 1684060 A1 | 7/2006 |
| JP | 08-043395 | 2/1996 |
| JP | H08-313539 A | 11/1996 |
| JP | 2006-170662 A | 6/2006 |
| WO | 2001/003721 A1 | 1/2001 |
| WO | 2002/076477 A1 | 10/2002 |
| WO | 2004/007528 A2 | 1/2004 |
| WO | 2007/120241 A2 | 10/2007 |
| WO | 2007/133710 A2 | 11/2007 |
| WO | 2014/145581 A1 | 9/2014 |
| WO | 2014/145619 A1 | 9/2014 |
| WO | 2017/015662 A1 | 1/2017 |
| WO | 2018/085151 A1 | 5/2018 |

OTHER PUBLICATIONS

International Search Report and Written Opinion for PCT/US2014/030373 dated Jul. 30, 2014.

International Search Report and Written Opinion for PCT/US2014/030414 dated Aug. 8, 2014.

International Search Report and Written Opinion for PCT/US2015/023408 dated Jul. 2, 2015.

Levy et al., In vitro methods for diagnosing allergy and directing therapy. US Respiratory Disease, vol. 6, pp. 63-67 (2010).

Sanchez-Guerrero et al. Utility of Anti-Sm, Anti-Ro/SS-A and Anti-La/SS-b (Extractable Nuclear Antigens) Detected by Enzyme-Linked Immunosorbent Assay for the Diagnosis of Systemic Lupus Erythematosus. Arthritis & Rheumatism, 39(6), pp. 1055-1061 (1996).

Sista et al., Heterogeneous immunoassays using magnetic beads on a digital microfluidic platform. Lab on a Chip, 8 (12):2188-2196 (2008).

Nichkova et al., Multiplexed immunoassays for proteins using magnetic luminescent nanoparticles for internal calibration. Analytical Biochemistry 369:34-40 (2007).

Communication pursuant to Rule 114(2) EPC—Third Party Observations—dated Feb. 15, 2019 for European Patent Application Serial No. 15887969.2.

Extended European Search Report dated Jul. 18, 2018 for European Patent Application Serial No. 15887969.2.

Machine translation of EP684475A2 corresponding to JP08-043395.

Nordengrun et al., The quest for bacterial allergens. International Journal of Medical Microbiology, vol. 308, No. 6, pp. 738-750 (2018).

Office Action for related case, European Patent Application Serial No. 14723936.2, dated Apr. 30, 2019.

Office Action for related case, Australian Patent Application Serial No. 2018220044, dated Jun. 18, 2019.

(56) References Cited

OTHER PUBLICATIONS

Office Action for related case, U.S. Appl. No. 15/482,460, dated Jun. 26, 2019.
Office Action for related case, U.S. Appl. No. 15/682,780, dated Jul. 10, 2019.

* cited by examiner

DEVICE AND ASSOCIATED METHODS FOR PERFORMING LUMINESCENCE AND FLUORESCENCE MEASUREMENTS OF A SAMPLE

CROSS-REFERENCE TO RELATED APPLICATIONS

This application claims priority to and the benefit as a continuation application of U.S. application Ser. No. 14/634,011, filed Feb. 27, 2015, entitled "Device and Associated Methods for Performing Luminescence and Fluorescence Measurements of a Sample", now U.S. Pat. No. 9,753,033, issued Sep. 5, 2017, which is a continuation of U.S. application Ser. No. 14/215,861, filed Mar. 17, 2014, entitled "Device and Associated Methods for Performing Luminescence and Fluorescence Measurements of a Sample", now U.S. Pat. No. 9,075,055, issued Jul. 7, 2015, which is related to and claims priority to U.S. Provisional Patent Application Ser. Nos. 61/791,295 and 61/791,879, each of which were filed on Mar. 15, 2013, the complete and entire disclosures of each of which are hereby expressly incorporated by reference herein.

BACKGROUND OF THE DISCLOSURE

The statements in this section merely provide background information related to the present disclosure and should not be construed as constituting prior art.

During an automated immunochemistry analysis, analyte molecules in a patient's biological sample (e.g. serum or plasma) attach to paramagnetic particles. To remove background signals associated with potential chemical sources that may be present in the sample as well, a number of washing steps are typically implemented into the process. A consequence of these washing steps, however, is that some fraction of the original particles will be lost for subsequent chemistry processes.

As such, there is a need for a process that allows the particles remaining after the washing steps to be quantified in order to normalize the luminescence signal from the patient sample. The present application is intended to improve upon and resolve some of these known deficiencies of the art.

SUMMARY OF THE DISCLOSURE

In accordance with one aspect of the present application, a process for optically measuring a dynamic chemical range of a sample in a reaction cuvette is provided. In accordance with this aspect of the present disclosure, the process comprises moving an optical detector from a luminescence reading position within a light tight optics box to a fluorescence reading position within the light tight optics box. By moving the optical detector to the fluorescence reading position, crosstalk from the fluorescence light source can be minimized.

According to another aspect of the present disclosure, an optical reading subassembly for an automated immunochemistry analyzer is provided and comprises an optical pipette configured to aspirate a sample from a cuvette as part of a chemistry process on an automated analyzer; an opaque optics box, which mates in a light tight manner with the optical pipette, with a common end and an emission end of a bifurcated optical fiber bundle, with a drain tube, and with a multi-pin electrical power/signal connector; a fluorescence excitation light source; a bifurcated fiber optic bundle, one leg of which is connected to the light source, one leg of which is connected through a series of emission optical filters to a fluorescence detection port of the optics box, and whose common end is connected to the optics box so that it can efficiently illuminate and thereby excite a fluorescent sample in the tip of the optical pipette and simultaneously collect a portion of the emission light from that fluorescent sample; a drain port, which allows droplets of fluid from the pipette tip to be removed from the optics box, without introducing stray light into the box; an optical detector with enough dynamic range to measure both fluorescence and luminescence signal from the samples; and a shutter mechanism, which can move the optical detector between a luminescence reading position, a fluorescence reading position, and an optically dark position.

In accordance with another aspect of the present disclosure, an apparatus for measuring the luminescence and the fluorescence of a sample is provided and comprises a light tight optics box capable of receiving a pipette tip containing a sample; an optical sensor located within the optics box and capable of being disposed in both a luminescence reading position and a fluorescence reading position; an excitation light fiber optic bundle and a sample transmission fiber optic bundle; an excitation light assembly that projects excitation light onto a first terminus end of the excitation light fiber optic bundle; and an in-line filter located along the sample transmission fiber optic bundle; wherein the optical sensor observes a luminescence reading from the sample while in the luminescence reading position and then transfers to the fluorescence reading position to project excitation light into one end of the excitation light fiber optic bundle, the excitation light fiber optic bundle being configured to transfer the excitation light onto the sample in the pipette tip; and wherein the transmission fiber optic bundle is configured to transmit the observed luminescence reading of the sample through the in-line filter and to the optical sensor disposed in the fluorescence reading position.

In accordance with still another aspect of the present disclosure, an automated method for controlling an automated fluorescence and luminescence reading device is provided and comprises the steps of moving an optics pipettor from a neutral position to a position within a cuvette; aspirating a sample from the cuvette; raising the optics pipettor out of the cuvette and positioning the sample at the tip of the optics pipettor by aspirating a volume of air; moving the optics pipettor to orient a clear tip of the optics pipettor within the internal region of an optics box; rotating an optical sensor from a second position to a first position via an electric motor; measuring and recording the luminescence reading from the optical sensor; rotating the optical sensor to a third position; enabling an excitation light emitting diode to project excitation light onto one terminus end of an excitation fiber optic bundle; projecting the excitation light from the excitation fiber optic bundle onto the sample; transmitting an observed reaction through a transmission fiber optic bundle to a transmission terminus end disposed across from the optical sensor; measuring and recording the fluorescence reading projected from the transmission terminus end onto the optical sensor; rotating the optical sensor to the second position; measuring and recording a dark reading while the optical sensor is in the second position; moving the optics pipettor from the optics box to a wash station; flushing the sample from the optics pipettor by dispensing a volume of air; aspirating a system liquid into the optics pipettor and dispersing the system liquid in a wash cycle; and moving the optics pipettor to the neutral position in preparation for the next sample.

In accordance with yet another aspect of the present disclosure, an automated fluorescence and luminescence reading machine is provided and comprises an optics pipettor that has a clear tip, an opaque body, and a disc feature around the opaque body; a pipette transfer arm that transfers the optics pipettor to a plurality of locations, the plurality of locations including a read position, a wash position, and a sample aspiration position; an optics box that can encompass a light tight internal environment when the optics pipettor is in the read position; a drain port coupled to the optics box, the drain port coupling to a drain tube that transfers any excess liquid out of the internal environment; a first fiber optic transition coupled to the optics box, the first fiber optic transition creating a light-tight seal to allow a first fiber optic bundle to expose an emission terminus end inside the internal environment; a second fiber optic transition coupled to the optics box, the second fiber optic transition creating a light-tight seal to allow a common terminus fiber optic bundle to expose a common terminus end inside the internal environment; a stepper motor coupled to a shutter mechanism; an optical sensor coupled to the shutter mechanism, the shutter mechanism and the stepper motor controlling the orientation of the optical sensor; an optical alignment plate containing a first reading position, a second reading position, and a third reading position; and a reentrant seal on the optics box, the reentrant seal designed to partially mate with the disc feature around the opaque body of the optics pipettor, a fluorescence excitation assembly that houses a light emitting diode, the light emitting diode configured to transmit a fluorescence signal to a terminus end of a fluorescence excitation fiber optic bundle; wherein when the pipette transfer arm transfers the optics pipettor to the read position, the reentrant seal and the disc feature may partially mate to one another to prevent light from entering the internal environment; and wherein when the pipette is in the read position, the optical sensor may be aligned in the first reading position where the luminescence reading of a sample within the clear tip may be measured by the optical sensor and when the optical sensor is aligned in the third reading position where a fluorescence measurement is obtained from the sample in the clear tip through the emission terminus end of the first fiber optic bundle.

BRIEF DESCRIPTION OF THE DRAWINGS

The above-mentioned aspects of the present invention and the manner of obtaining them will become more apparent and the invention itself will be better understood by reference to the following description of the embodiments of the invention taken in conjunction with the accompanying drawings, wherein.

Figure 1:
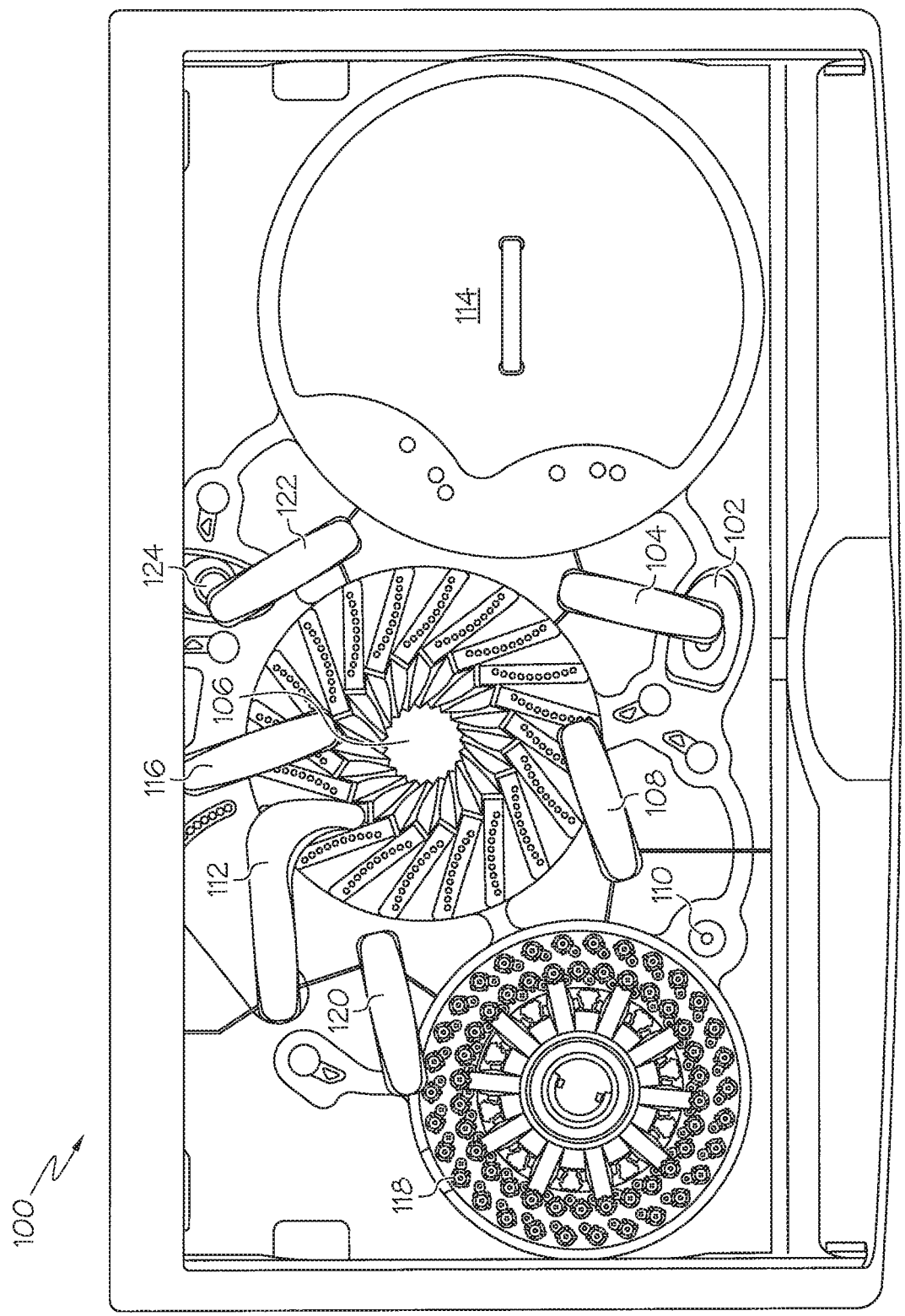
FIG. 1 is a top schematic view of an automated immunochemistry analyzer and reagent system in accordance with the teachings of the present application.

Corresponding reference characters indicate corresponding parts throughout the several views. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION

The above-mentioned aspects of the present application and the manner of obtaining them will become more apparent and the teachings of the present application itself will be better understood by reference to the following description of the embodiments of the present application. Moreover, although the exemplification set out herein illustrates embodiments of the present application, in several forms, the embodiments disclosed below are not intended to be exhaustive or to be construed as limiting the scope of the present application to the precise forms disclosed. Rather, the embodiments are chosen and described so that others skilled in the art may appreciate and understand the principles and practices of the present application.

Unless defined otherwise, all technical and scientific terms used herein have the same meaning as commonly understood by one of ordinary skill in the art to which this application belongs. Although any method and materials similar or equivalent to those described herein can be used in the practice or testing of the present application, the specific methods and materials are now described.

FIG. 1 illustrates the various components of an automated diagnostic immunochemistry analyzer 100 in accordance with the teachings of the present disclosure. The automated immunochemistry analyzer 100 can take an analyte sample, create an environment that will allow it to bind to a paramagnetic particle, perform a number of washing steps, then quantify and normalize the luminescence signal of the analyte sample. This can be accomplished through an automated process that utilizes a vortexer 102, an R1 pipettor 104, a reaction rotor 106, an optics pipettor 108, an optics box 110, a multi rinse pipettor 112, a reagent rotor 114, a single rinse pipettor 116, a sample rotor 118, a sample pipettor 120, an R2 pipettor 122, and a mixed substrate container 124.

To better understand the mechanical aspects of this disclosure, a sample process will be outlined explaining one possible method the apparatus could utilize to quantify and normalize the luminescence signal of an analyte sample. Specifically, the automated immunochemistry analyzer 100 begins by first dispensing fluorescently labelled paramagnetic particles, or fluo-beads, into a cuvette located within the reaction rotor 106. The fluo-beads may initially be located in the vortexer 102 and be transferred to the reaction rotor 106 by the R1 pipettor 104. The R1 pipettor 104 can aspirate a desired quantity of the fluo-bead mixture and transfer the aspirated quantity to the reaction rotor 106 where it is injected into the cuvette of the reaction rotor 106. Following the injection into the cuvette, the optics pipettor 108 may aspirate a test sample from the cuvette of the reaction rotor 106 and transfer the test sample to the optics box 110. Once the sample is disposed within the optics box 110, fluorescence and luminescence measurements can be recorded. The initial recording of the fluorescence and luminescence signal can be used as a baseline measurement for the fluorescence signal that can correspond to the initial concentration of fluo-beads in a sample. After recording the measurements, the multi rinse pipettor 112 can rinse the cuvettes using a wash buffer.

Next, fluo-beads may be transferred from the vortexer 102 to a cuvette in the reaction rotor 106 via the R1 pipettor 104. Then, the R1 pipettor 104 may aspirate a capture reagent from the reagent rotor 114 and inject the capture reagent into the cuvette located in the reaction rotor 106. After an incubation period, the single rinse pipettor 116 may inject a rinse buffer to resuspend the fluo-bead. A substantial amount of the suspended fluo-bead may then be localized by magnets within the reaction rotor 106 over a period of time. After the magnets have substantially localized the fluo-beads within the cuvette, the multi rinse pipettor 112 may aspirate and dispose of a portion of the rinse buffer, leaving a portion of the fluo-beads localized within the cuvette. The multi rinse pipettor 112 may proceed to inject a wash buffer into the cuvette of the reaction rotor 106, resuspending the fluo-beads. The fluo-beads may again be localized by the magnets within the reaction rotor 106 to be followed by the multi rinse pipettor 112 aspirating and discarding a portion of the sample that was not localized from the cuvette in the reaction rotor 106.

A patient sample may be contained in a sample tube on in the sample rotor 118. The patient sample may further be partially diluted with a sample diluent. At this point, the sample pipettor 120 may aspirate a portion of the patient sample and inject the patient sample into the cuvette of the reaction rotor 106 to resuspend the fluo-beads. The cuvette containing the patient sample within the reaction rotor 106 may then incubate the patient sample. In one embodiment, the incubation temperature can be about 37 degrees Celsius+/−about 0.2 degree Celsius while the incubation time can be about 37.75 minutes+/−about 2 minutes. After incubation, the single rinse pipettor 116 may inject the rinse buffer to again resuspend the fluo-beads. Another localization process is performed by the reaction rotor 106 by allowing the fluo-beads to substantially collect within the cuvette near the magnets in the reaction rotor 106. After the localization of the fluo-beads, the multi rinse pipettor 112 may aspirate and discard a portion of the fluid within the cuvette of the reaction rotor 106 that was not localized during the localization process.

A couple of rinse cycles may then be performed on the sample within the cuvette of the reaction rotor 106. The rinse cycle may comprise using the multi rinse pipettor 112 to inject a wash buffer into the cuvette to resuspend the fluo-beads. Another localization step may allow the fluo-beads to collect within the cuvette by the magnets within the reaction rotor 106. After about a 90 second fluo-beads collection period, the multi rinse pipettor 112 may aspirate and discard a portion of the wash buffer, leaving a substantial portion of the fluo-beads within the cuvette of the reaction rotor 106. Another rinse cycle may then occur by using the multi rinse pipettor 112 to again inject wash buffer into the cuvette and allow the fluo-beads to resuspend. Another fluo-bead localization process may utilize the magnets within the reaction rotor 106 to localize the fluo-beads from the rest of the sample. Finally, the multi rinse pipettor 112 may aspirate a portion of the sample that was not localized by the localization process.

At this point, the R2 pipettor 122 may aspirate a conjugate contained in a conjugate cuvette within the reagent rotor 114. The R2 pipettor 122 may then inject the previously aspirated conjugate into the cuvette of the reaction rotor 106. After incubating the cuvette under controlled time and temperature in the reaction rotor 106, the single rinse pipettor 116 may inject a rinse buffer into the cuvette in the reaction rotor 106. Another fluo-bead localization cycle may be performed by allowing magnets within the reaction rotor 106 to substantially localize the fluo-beads within the cuvette. The multi rinse pipettor 112 may aspirate and discard a portion of the sample within the cuvette that has not been localized during the localization cycle.

Two more rinse cycles may be performed on the sample within the cuvette of the reaction rotor 106. The multi rinse pipettor 112 may inject a wash buffer to resuspend the fluo-beads within the cuvette. Another fluo-bead localization cycle may localize the fluo-beads by locating the cuvette within close proximity to the magnets in the reaction rotor 106 over an adequate period of time. After the localization cycle, the multi rinse pipettor 112 may aspirate and discard a portion of the sample that was not localized during the localization cycle. A second wash cycle may then occur by using the multi rinse pipettor 112 to inject the wash buffer to resuspend the fluo-beads. Another localization cycle may utilize the magnets within the reaction rotor 106 to localize the fluo-beads within the cuvette. After the localization process, the multi rinse pipettor 112 may again aspirate and discard a portion of the sample that was not localized during the localization cycle.

At this point, the R2 pipettor 122 may aspirate a portion of conjugate from the reagent rotor 114 and inject the conjugate into the mixed substrate container 124 creating a mixed substrate sample. The R2 pipettor may then aspirate the mixed substrate sample from the mixed substrate container 124 and inject the mixed substrate sample into the cuvette of the reaction rotor 106, resuspending the fluo-bead with the mixed substrate sample. The sample in the cuvette of the reaction rotor 106 may then be aspirated by the optics pipettor 108 and placed in the optics box 110. After the optics box makes fluorescence and luminescence optical observations, the sample is discarded and the multi rinse pipettor rinses the cuvettes of the reaction rotor 106 in preparation for the next test.

Figure 2:
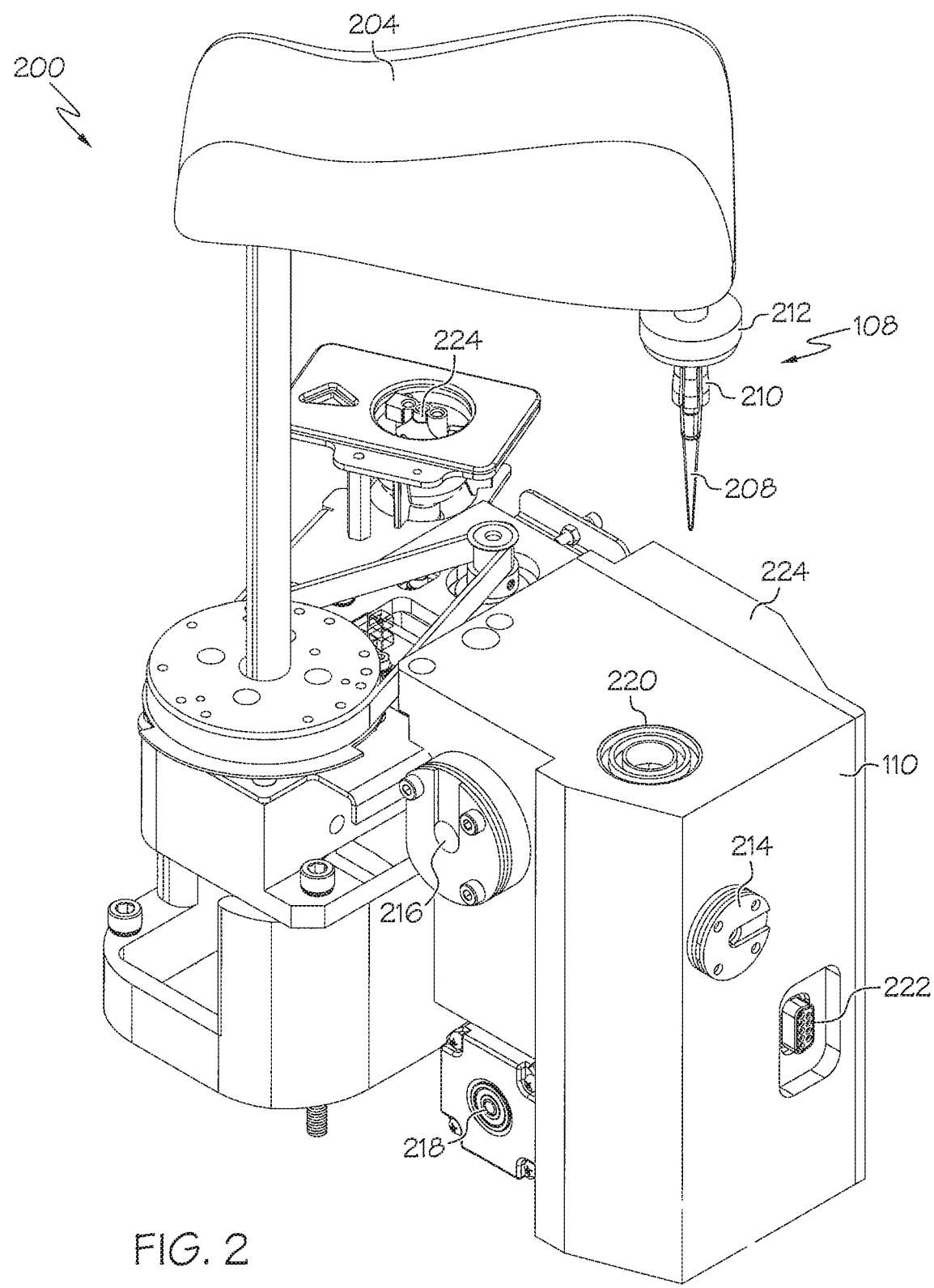
FIG. 2 is a perspective view of the optical subassembly of the automated immunochemistry analyzer and reagent system of FIG. 1.

Moving now to FIG. 2, an optical subassembly 200 of the automated immunochemistry analyzer and reagent system 100 is described in more detail. More particularly, the optics pipettor 108 is shown coupled to a pipette transfer arm 204. The optics pipettor 108 may be composed of a substantially opaque body 210 and terminate at a substantially clear tip 208. Further, the optics pipettor 108 may have a disc feature 212 located along the opaque body 210. The optics pipettor 108 and the pipette transfer arm 204 may be mechanically coupled to one another in a way that allows the optics pipettor 108 to be transferred to and from a plurality of positions with respect to the automated analyzer 100. For example, the optics pipettor 108 could be transferred from the optics box 110 to a wash station 224, from the wash station 224 to the reaction rotor 106, from the reaction rotor 106 to the optics box 110, or any combination thereof.

The optical subassembly 200 is a robotic device that can access a cuvette on the reaction rotor 106 of the automated immunochemistry analyzer 100, aspirate a sample to a controlled position within the optically clear tip 208, and position the clear tip 208 to a controlled position within the optics box 110. Except for the clear tip 208, which is optically clear, the opaque body 210 connected to it is opaque in order to not introduce stray light into the optics box 110. The disc feature 212 of the opaque body 210 may mate in a reentrant fashion with the optics box 110 in order to prevent stray light from entering the box. The opaque body 210 can be any non-compliant material, such as, but not limited to, black FEP, a black polymer (e.g., Delrin or ABS) that can be machined to permit airtight mating with the clear tip 208. The clear tip 208 can be any optically clear polymer, such as, but not limited to, polypropylene. While various different materials can be used for the clear tip 208, it should be understood and appreciated by those within the art that care should be taken to avoid materials that might fluoresce or luminesce at the excitation wavelength used in the device.

The pipette transfer arm 204 may be capable of placing the clear tip 208 of the optics pipettor 108 at least partially inside the optics box 110, allowing the disc feature 212 to become partially disposed within an optics pipettor reentrant seal 220 located on the optics box 110. When the disc feature 212 is at least partially disposed within the optics pipettor reentrant seal 220, light is substantially inhibited from entering the optics box 110.

Figure 3:
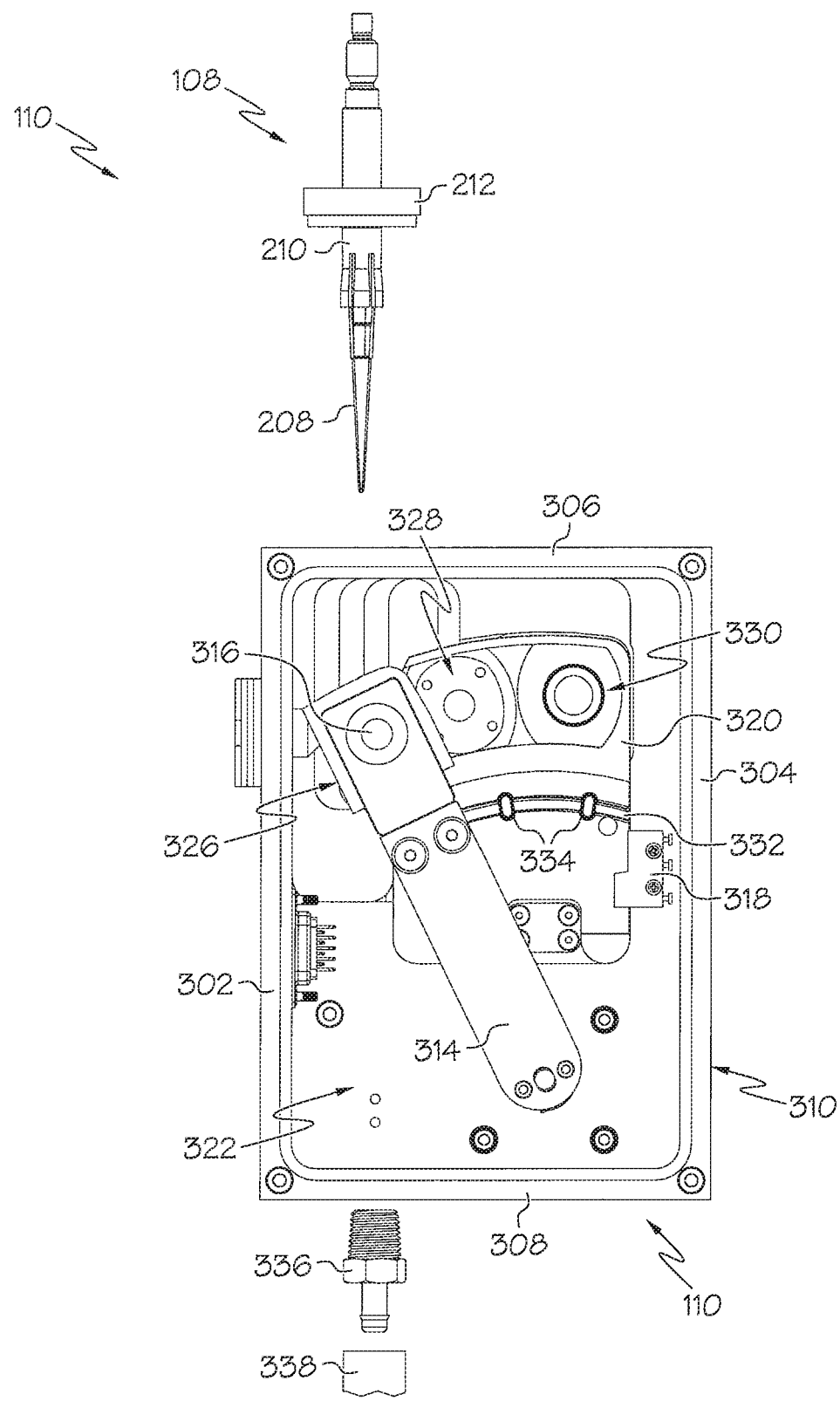
FIG. 3 is a front side view of a portion of the optical subassembly of FIG. 2 with a front surface removed.

The optics box 110 is an enclosure with several ports for optical, electrical, and mechanical connections. Care must be taken so that all such connections permit no stray light to enter the box. In particular, the port for the optics pipettor 108 has the disc feature 212 that mates with the reentrant feature of the optics box 110. In one embodiment, the optics box 110 is made from a polymer material (such as black ABS) that can be easily machined to discourage reflectance by surface roughening, painting, or other such means. It may contain features, such as light traps or baffles that minimize the stray light entering the optical sensor. It provides well-defined unobstructed optical paths for the fluorescence and luminescence readings. It has a drain port opaque fitting 336 and tubing 338 that are connected to the optics box 110 and permits any liquid that might drip from the optics pipettor 108 to pool and be carried away from the region of optical detection (FIG. 3). The optics box 110 has a provision for mounting a drive mechanism (such as, but not limited to, a stepper motor) and a sensor for a shutter mechanism. The optics box 110, in accordance with one embodiment, has detent features for accurately positioning the optical sensor for luminescence and fluorescence reading.

Figure 12:
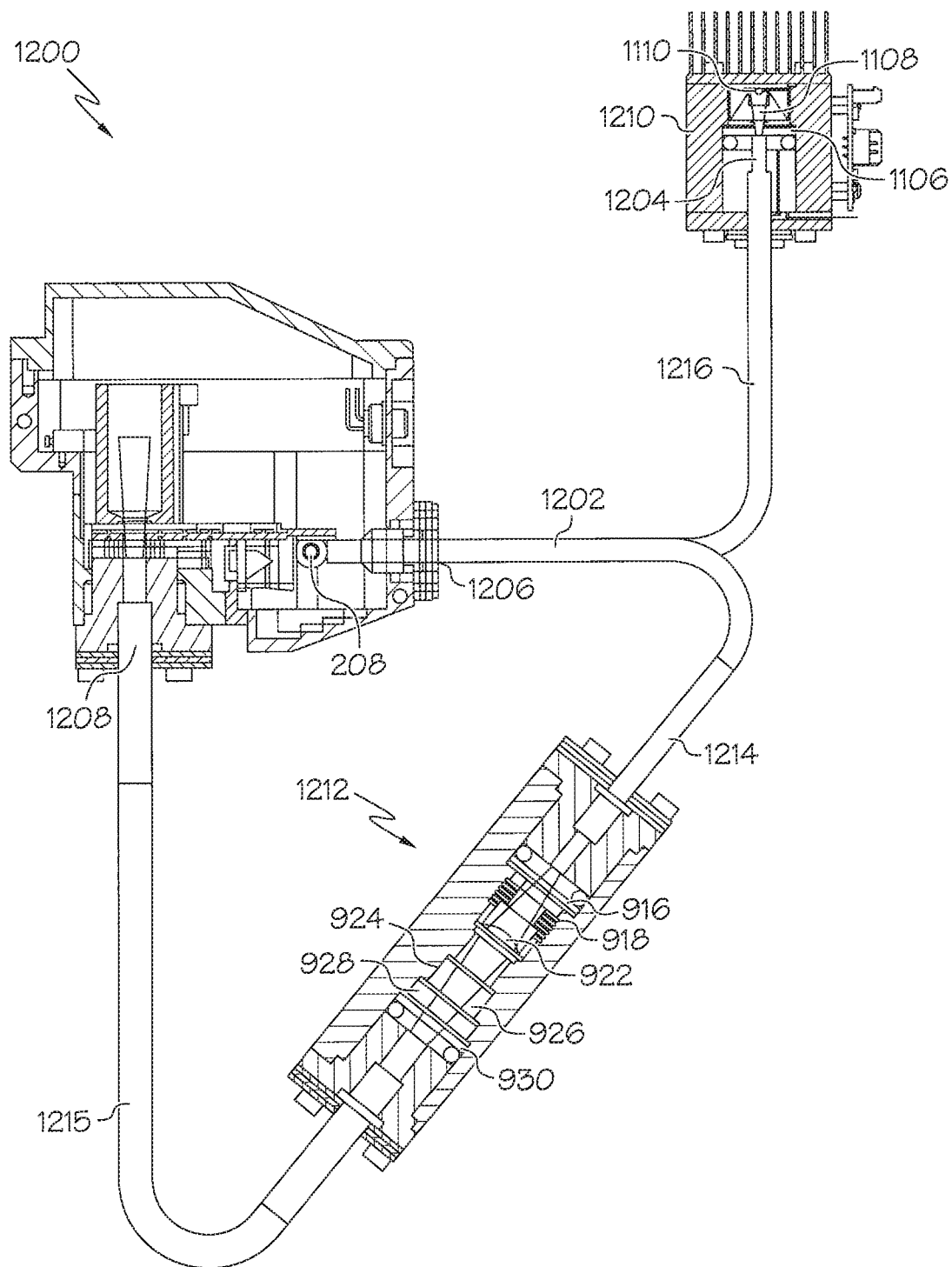
FIG. 12 is a top side section view of a bifurcated fiber optic cable routing system in accordance with the teachings of the present application.

FIG. 2 further illustrates a fiber optic cable common terminus inlet 214 and a fiber optic cable emission terminus inlet 216. Both the fiber optic cable common terminus inlet 214 and the fiber optic cable emission terminus inlet 216 can provide a light-sealed transition between the interior of the optics box 110 and the exterior of the optics box 110 for a bifurcated fiber optic cable 1202 (FIG. 12). The fiber optic cable inlets 214, 216 can allow only desired light signals to be distributed into, and transferred out of the optics box 110.

Further, a shutter stepper motor 218 may be coupled to the optics box 110 with a light-tight seal similar to the reentrant seal 220, allowing the shaft of the shutter stepper motor 218 to be disposed within the interior of the optics box 110 without allowing any external light to penetrate through the mounting location. One skilled in the art can appreciate the many ways such a seal could be achieved. For example, the body of the shutter stepper motor 218 could be coupled to the optics box and a gasket or O-ring could be positioned between the body of the shutter stepper motor 218 and the optics box 110, preventing any exterior light from entering the interior portion of the optics box 110 at the seal. Further, a reentrant seal could utilize a series of circular peaks and valleys about the opening on the optics box 110 that mate to inverse peaks and valleys located on the shutter stepper motor 218. One skilled in the art can understand that the light tight seal between the shutter stepper motor 218 and the optics box 110 can be achieved many different ways and the present disclosure should not be limited to the particular methods disclosed above.

An electronics communication coupler 222 may also be located on the optics box 110. The electronics communication coupler 222 can allow an external electrical connector to be electronically coupled to any electrical devices inside the optics box 110. For instance, the electronics communication coupler 222 could allow a system controller to become electronically coupled too, and thereby control, the electrical components within the optics box 110. Further the electronics communication coupler 222 can provide a light tight transition for wired electronic signals from the inside of the optics box 110 to the outside of the optics box 110 or vice versa. The electronics communication coupler 222 may also be coupled to the optics box 110 in a plurality of ways that inhibit outside light infiltration. More specifically, the electronic communication coupler 222 can be coupled to the optics box 110 with opaque adhesives that may hold the electronic communications coupler 222 in place while simultaneously preventing any exterior light from entering the optics box 110. Further, a gasket or O-ring may be disposed between the optics box 110 and the electronic communications coupler 222 to prevent any external light from entering the interior of the optics box 110.

FIG. 3 shows a more detailed view of the optics box 110 with one surface removed. The optics box 110 may be comprised of a first section 302, a second section 304, a third section 306, a fourth section 308, a fifth section 310, and a cover section 226 (FIG. 2). Each of the sections 302, 304, 306, 308, 310, and 226 may be coupled to one another in a way that creates an internal area 322 that is substantially isolated from any external light by implementing any of a plurality of methods for creating a light-tight seal. One skilled in the art could understand the many possible methods for coupling sections together in a light tight manner can be utilized in accordance with the present disclosure, whereby the present teachings are not intended to be limited herein. For instance, in accordance with certain aspects, a gasket can be placed at every coupled edge, providing a tongue-and-groove relationship between the sections. Alternatively, the sections could be welded or machined in such a manner that the infiltration of outside light is substantially restricted.

The drain port opaque fitting 336 in the optics box 110 may be located beneath the optics pipettor 108 so that any liquid dripping from the clear tip 208 could accumulate in or above the drain port opaque fitting 336 and be removed from the box by gravity or by an external pump through the tubing 338. To prevent stray light from entering the optics box 110, the drain port opaque fitting 336 and tubing 338 can be substantially resistant to external light permeation. Maintaining the light tight seal of the internal portion of the optics box 110 may further be achieved by having the tubing 338 extend away from the optics box 110 in a corkscrew fashion. The corkscrew path of the tubing 338 may ensure there is no direct path for any external light to shine into then optics box 110 through the tubing 338. Further, the interior of the tubing 338 may be made of a non-reflective material that can substantially restrict the transmission of light through the interior portion of the tubing 338. While one embodiment utilizes a corkscrew configuration of the tubing 338, one skilled in the art would appreciate how many tubing configurations could be used to prevent light from having a direct path to the interior of the optics box. For instance, a zigzag, semicircular arc, or 90 degree bend among other things could be used in the tubing 338 to restrict light from entering the optics box 110 and this disclosure should not be limited to any particular orientation.

The internal area created by the surrounding sections 302, 304, 306, 308, 310, and 226 may also contain a shutter mechanism 314, an optical sensor 316, a shutter sensor 318, and an optical alignment plate 320 among other things. The third section 306 may contain the optics pipettor reentrant seal 220 for the optics pipettor 108. The clear tip 208 of the optics pipettor 108 may be substantially disposed within the internal area 322 when the disc feature 212 is at least partially coupled to the optics pipettor reentrant seal 220. The disc feature 212 may be spaced an appropriate distance from the clear tip 208 to ensure that when the disc feature 212 contacts the optics pipettor reentrant seal 220 the clear tip 208 will be disposed in a desired location for making an optical reading. Further, the optics pipettor reentrant seal 220 may have a series of circular peaks and valleys that inversely correlate with the corresponding portion of the disc feature 212. When the disc feature 212 is at least partially disposed within the optics pipettor reentrant seal 220 of the third section 306, the peaks and valleys of the disc feature 212 and the optics pipettor reentrant seal 220 at least partially couple to one another to substantially block any exterior light from entering the internal area 322 of the optics box 110.

The optical sensor 316 may be coupled to the shutter mechanism 314 which is in turn coupled to the shutter stepper motor 218. The optical sensor 316 may be oriented so that the measurement side of the optical sensor 316 is oriented towards the optical alignment plate 320. The optical sensor 316 can be used to measure both fluorescence and luminescence signals from a source. In one embodiment, the optical sensor may be a photomultiplier tube. The optical sensor 316 may also be sensitive to light and require the internal area 322 to be substantially void of any light other than the light emitted from the desired source.

The optical alignment plate 320 can contain a plurality of reading positions for the optical sensor 316. In the embodiment shown in FIG. 3, the optical alignment plate 320 contains three reading positions. In particular, a first reading position 326 could be for the luminescence reading of a sample within the clear tip 208. A second reading position 328 could be substantially blank and allow for a closed position that enables dark current and other electronic background measurements to be obtained. A third reading position 330 could be for a fluorescence reading transmitted through fiber optic cables.

Because the luminescence signals from samples may be quite low, a high sensitivity optical detector, such as a photomultiplier tube (PMT), may be used. In the first reading position 326, or the luminescence reading position, the PMT is in close proximity to the sample within the clear tip 208 and therefore accepts a significant fraction of the luminescence photons emitted from the sample. In the third reading position 330, or the fluorescence reading position, the PMT is in close proximity to one end of the receiving fiber bundle and captures most of the emission light emanating from its tip. In addition to the fluorescence and luminescence reading positions, the PMT can be placed in the second reading position 328, or an optically isolated position, where dark current and other electronic background measurements can be obtained.

The optical sensor 316 could be transitioned to and from each of the reading positions 326, 328, and 330 by the shutter mechanism 314. The shutter mechanism 314 could be coupled to a stepper motor, a pneumatic arm, or any other comparable mechanism that could allow for the movement of the optical sensor 316. The shutter mechanism 314 may also be in communication with the shutter sensor 318. The shutter sensor 318 may monitor the orientation of the shutter mechanism 314 and confirm or dictate desired movements of the shutter mechanism 314. The shutter sensor 318 can confirm that the optical sensor 316 is accurately aligned with any one of the plurality of reading positions 326, 328, and 330 on the optical alignment plate 320.

To further facilitate accurate optical readings, a cam system can be utilized between the shutter mechanism 314 and the optical alignment plate 320. The cam system can allow the optical sensor 316 to be separated from, and coupled to, a reentrant seal located at each of the reading positions 326, 328, and 330 as the optical sensor 316 transitions from one reading position to the other. The cam system can incorporate a U-shaped channel 332 disposed within the surface of the optical alignment plate 320. The U-shaped channel 332 can follow an arc along the surface of the optical alignment plate 320 that is concentric with the pivotal center of the shutter stepper motor 218 shaft. The U-shaped channel 332 may further have a detent or detents 334 located at the second reading position 328 and the third reading position 330. The detent or detents 334 may create a slightly greater recess in the optical alignment plate 320 than does the U-shaped channel 332. While one embodiment may only show the detent or detents 334 at the second reading position 328 and the third reading position 330, one skilled in the art can understand how the first reading position 326 could also have a detent and a U-shaped channel leading thereto.

Figure 4:
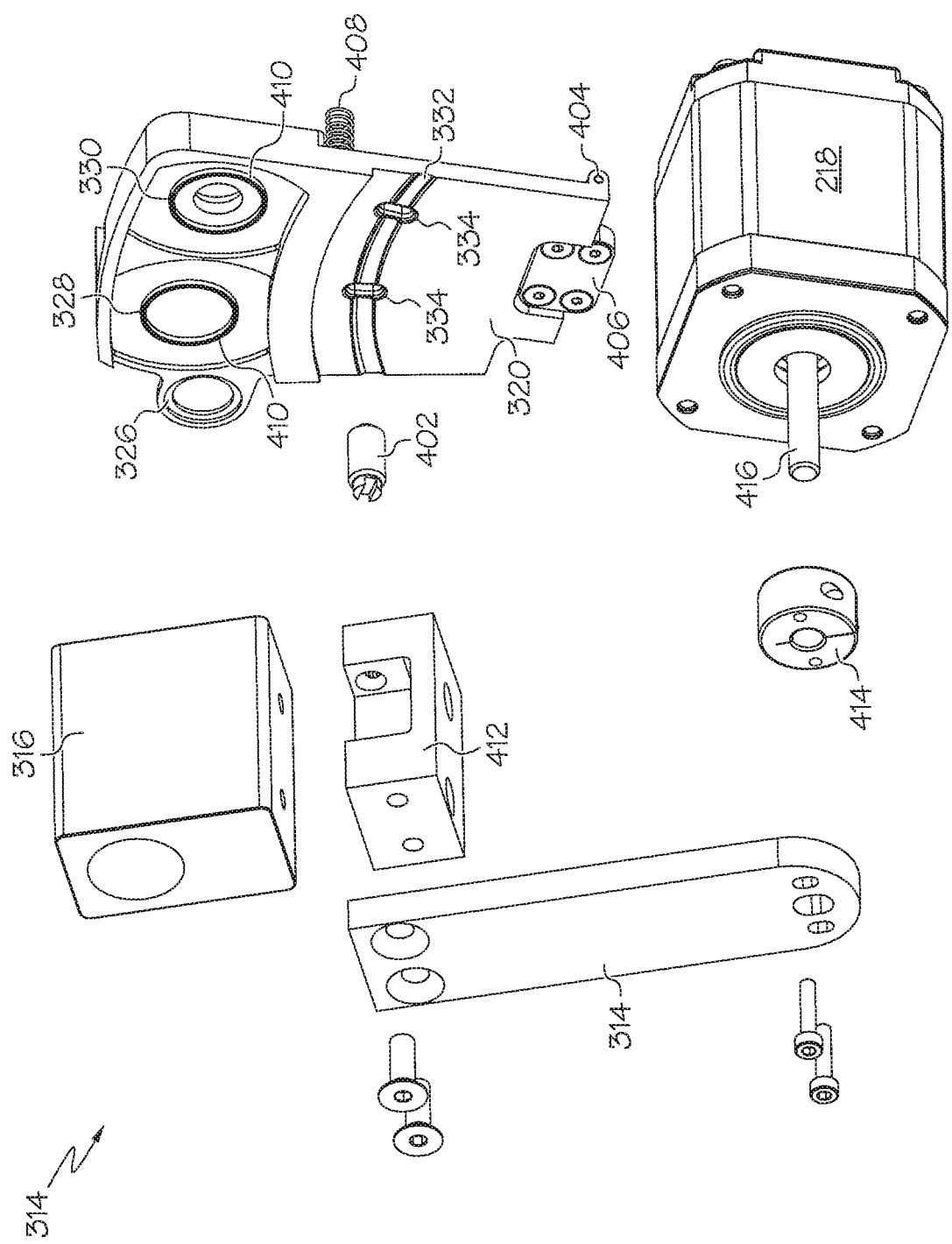
FIG. 4 is an exploded perspective view of some of the internal components of the portion of the optical subassembly of FIG. 3.

FIG. 4 shows the shutter assembly 314 in an exploded view with the optics box 110 removed. The optical alignment plate 320 may be pivotable about a pivot pin 404. Further, the pivot pin 404 may be coupled to the interior portion of the fifth section 310 by a pivot pin retention plate 406. The relationship between the pivot pin 404, the pivot pin retention plate 406, and the optical alignment plate 320 could be such that the optical alignment plate 320 may rotate about the axis of the pivot pin 404. The optical alignment plate 320 may also be coupled to one or more spring 408. The one or more spring 408 may have a first end that is coupled to the optical alignment plate 320 at a location on the opposite side as the U-shaped channel 332 and a second end that is coupled to an interior portion of the fifth section 310.

The U-shaped channel 332 may interact with a cam pin 402 located on a shutter mechanism coupler 412 to maintain the particular orientation between the optical alignment plate 320 and the optical sensor 316. More specifically, when the cam pin 402 is disposed in the U-shaped channel 332, the cam pin 402 may maintain a slight gap between the optical alignment plate 320 and the optical sensor 316. However, when the cam pin 402 enters the detent or detents 334, the optical alignment plate 320 may rotate towards the optical sensor 316 about the axis of the pivot pin 404. Once the cam pin 402 is at least partially located in the detent or detents 334, the optical alignment plate 320 may become oriented a sufficient distance from the optical sensor 316 to allow the optical sensor 316 to contact a photo sensor seal 410 around any of the first, second, or third reading positions 326, 328, and 330. As the shutter mechanism 314 repositions the optical sensor 316, the cam pin 402 may exit the detent or detents 334 and slightly rotate the optical alignment plate 320 away from the optical sensor 316 about the pivot pin 404 axis. The transition of the cam pin 402 out of the detent or detents 334 and into the U-shaped channel 332 may slightly compress the one or more spring 408 and allow the optical sensor 316 to no longer contact the photo sensor seal 410. The cam pin 402 may then continue to move along the U-shaped channels 332 of the optical alignment plate 320 until it reaches the next detent or detents 334. Further, while in the embodiment of the shutter mechanism 314 no detent is shown to orient the optical sensor 316 in the first reading position 326, the optical alignment plate 320 may terminate at a location that allows the cam pin 402 to become disposed off of the optical alignment plate 320 when the optical sensor is in the first reading position 326. Similarly to moving into and out of the detent or detents 334, the cam pin may move off of, or on to the optical alignment plate 320 to orient the optical sensor 316 between the reading positions 326, 328, and 330.

The shutter mechanism 314 may be coupled to the shutter stepper motor 218 by a hub 414. The hub 414 may be substantially cylindrical with an inner through hole that may be slightly greater than a stepper motor shaft 416 outer diameter. The hub 414 may also have a means for compressibly coupling the hub 414 to the stepper motor shaft 416. Further, the hub 414 may have at least one through hole that is parallel to the inner through hole that allow the hub 414 to be removably coupled to the shutter mechanism 314. When the hub 414 is compressibly coupled to the stepper motor shaft 416, and the shutter mechanism 314 is coupled to the at least one through hole of the hub 414, the shutter stepper motor 218 may substantially control the movement of the shutter mechanism 314.

The end of the shutter mechanism 314 that is opposite of the hub 414 may be coupled to the shutter mechanism coupler 412. The shutter mechanism coupler 412 may further couple the optical sensor 316 to the shutter mechanism 314. Finally, the cam pin 402 may be coupled to a shutter mechanism coupler 312 to ensure proper alignment between the optical alignment plate 320 and the optical sensor 316. The shutter mechanism 314 can allow the optical sensor 316 to measure luminescence and fluorescence signals from a single sample while minimizing cross-talk from the fluorescence excitation light source.

Figure 5:
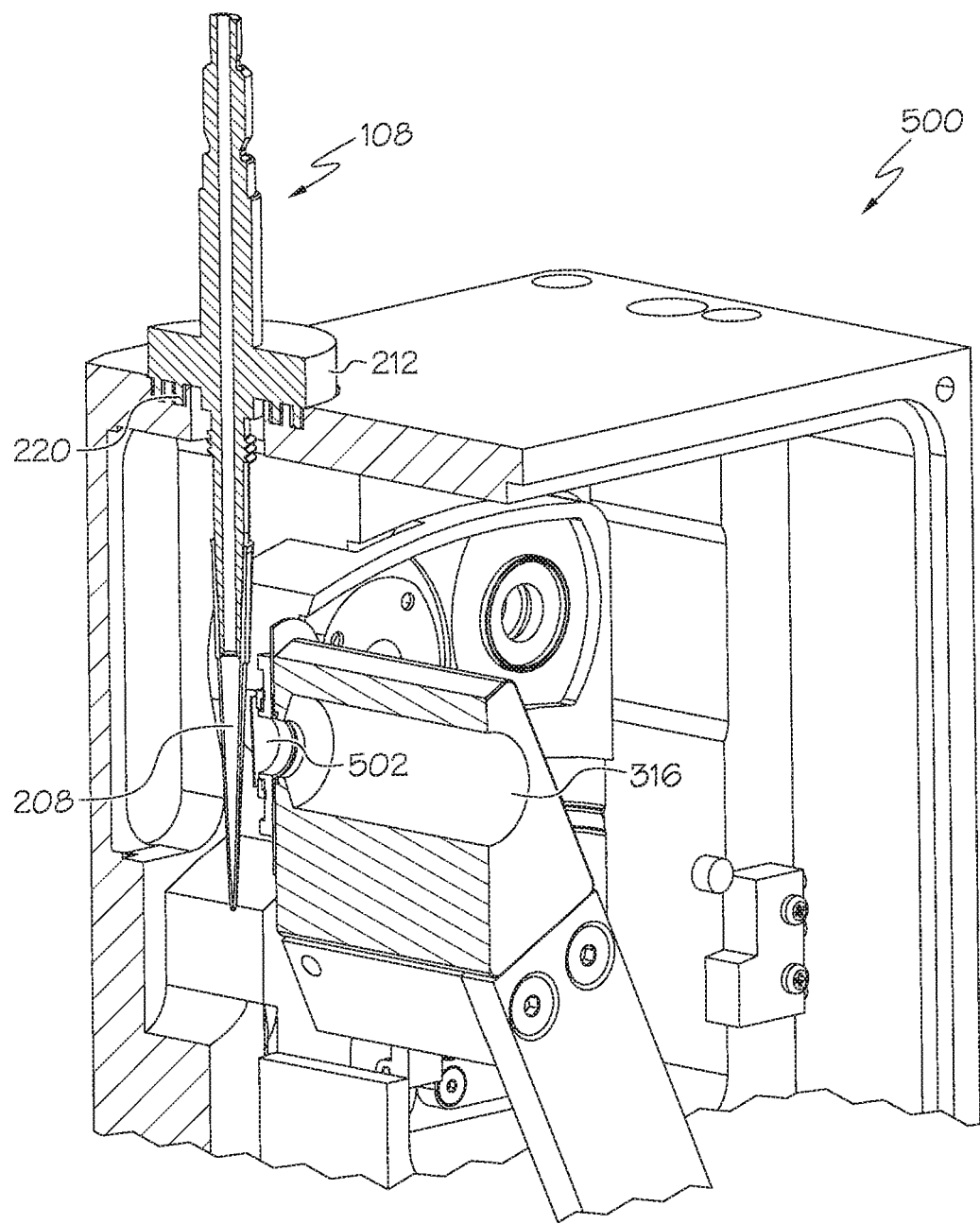
FIG. 5 is a partial section view of the portion of the optical subassembly of FIG. 3 with an optical sensor in a first position and an optical pipettor disposed therein.

FIG. 5 illustrates a partial cross section view 500 of the optical sensor 316 in the first reading position 326 with the disc feature 212 of the optics pipettor 108 at least partially coupled to the optics pipettor reentrant seal 220. In the first reading position 326, the optical sensor 316 may be disposed in a close proximity to the clear tip 208 of the optics pipettor 108. The optical alignment plate 320 may also house the photo sensor seal 410 and a neutral density optical filter 502 at the first reading position 326. The neutral density optical filter 502 may be disposed between the clear tip 208 and the optical sensor 316 where the neutral density optical filter 502 may adjusts the optical signals to be in the optical dynamic range of the optical sensor 316.

The close proximity of the optical sensor 316 to the clear tip 208 may allow the optical sensor 316 to analyze the luminescence of a sample located within the clear tip 208 of the optics pipettor 108. During the luminescence reading, it is crucial that the amount of background light is reduced to a minimum. Background light can be any undesired light that may enter the optics box 110 from an external source. By substantially limiting the amount of background light permitted into the optics box 110, the consistency and accuracy of the luminescence reading is greatly enhanced. FIG. 5 more clearly illustrates how the disc feature 212, the optics pipettor reentrant seal 220, and the opaque body 210 can substantially reduce the amount of background light that may enter the optics box 110 when the optics pipettor 108 is located therein.

In the second reading position 328, the optical sensor 316 may be substantially disposed in a closed position wherein the optical alignment plate 320 does not contain a through hole and thereby blocks the reading end of the optical sensor 316. In the second reading position 328, the optical sensor 316 may be substantially isolated from any form of illumination. This reading position may be advantageous because it may allow for dark current and other electronic background measurements to be obtained and used to aid in the calibration and accuracy of the desired measurements.

Figure 6:
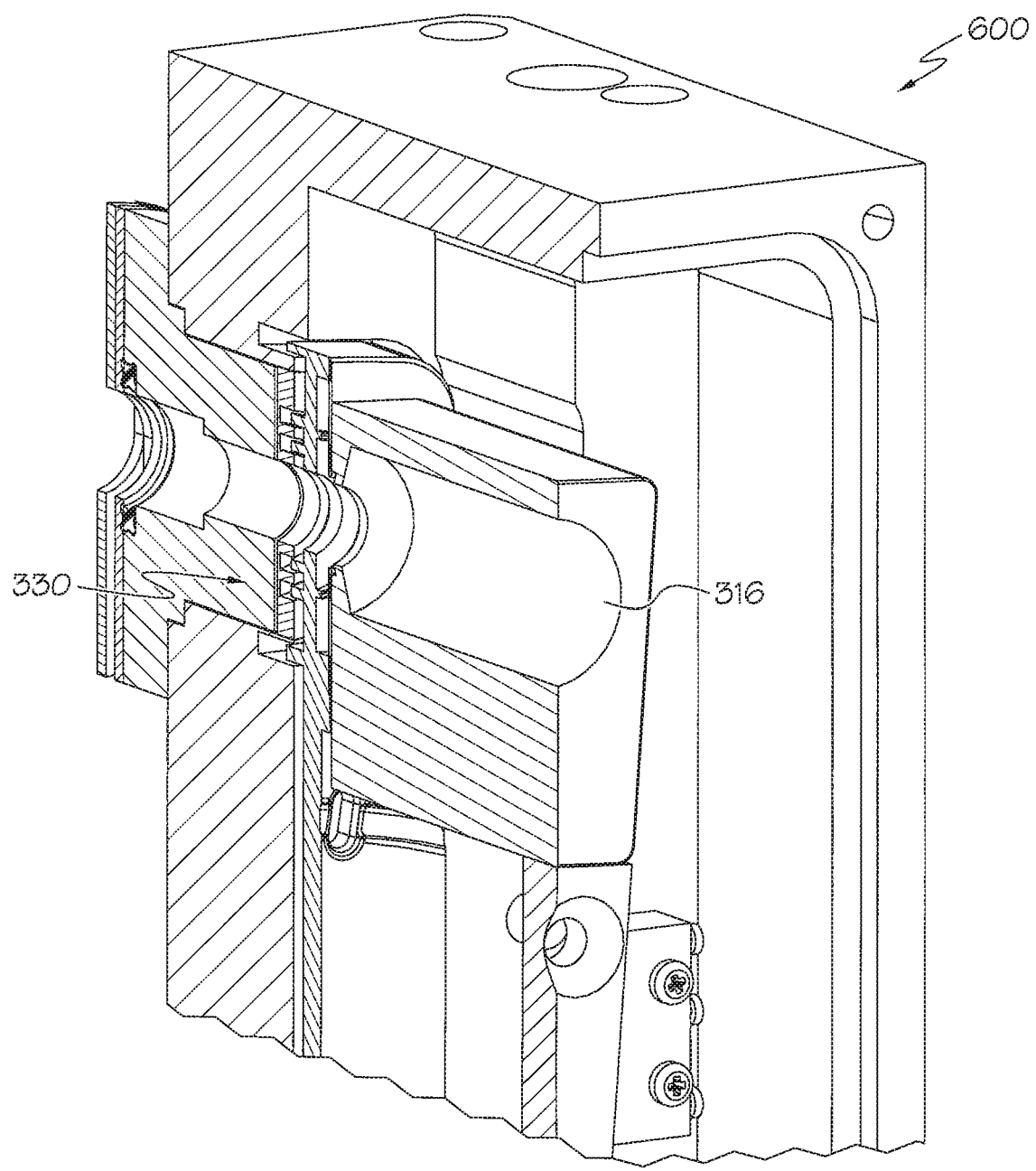
FIG. 6 is a partial section view of the portion of the optical subassembly of FIG. 3 with the optical sensor in a third position.

FIG. 6 shows a perspective partial sectional view 600 with the optical sensor 316 in the third reading position 330. FIG. 12 further shows how in the third reading position 330, the bifurcated fiber optic cable 1202 may be utilized to distribute fluorescence excitation light to and from desired locations 1200. More specifically, the bifurcated fiber optic cable 1202 may consist of a plurality of fiber optic fibers and may have an emissions fiber optic cable bundle 1216 that connects a common terminus end 1206 to a fluorescence excitation emission end 1204. Further, a first transmission fiber optic cable bundle 1214 can connect the common terminus end 1206 to a fiber optic filter housing 1212, while a second transmission fiber optic cable bundle 1215 can connect the fiber optic filter housing 1212 to a transmission end 1208. The common terminus end 1206 may be composed of a random configuration of fiber optic fibers from both the fluorescence excitation emission end 1204 and fiber optic fibers from the transmission end 1208. Further, in one embodiment there may be slightly more fiber optic fibers in the transmission end 1208 than in the fluorescence excitation emission end 1204. FIG. 6 shows how in the third reading position 330, the optical sensor 316 can be aligned with the terminus portion of the transmission end 1208 of the bifurcated fiber optic cable 1202. This alignment may allow the optical sensor 316 to accurately read the transmissions of the transmission end 1208 of the bifurcated fiber optic cable 1202.

The fluorescence excitation emission end 1204 can be at least partially disposed within a fluorescence excitation emission source housing 1210. The fluorescence excitation emission source housing 1210 could house a system for emitting a fluorescence excitation light source onto the fluorescence excitation emission end 1204 of the bifurcated fiber optic cable 1202. When fluorescence light is emitted onto the fluorescence excitation emission end 1204, the fluorescence excitation light may be transferred through the bifurcated fiber optic cable 1202 to the common terminus end 1206. At the common terminus end 1206, the fluorescence excitation light may be projected onto a sample located within the clear tip 208 of the optics pipettor 108.

Figure 7:
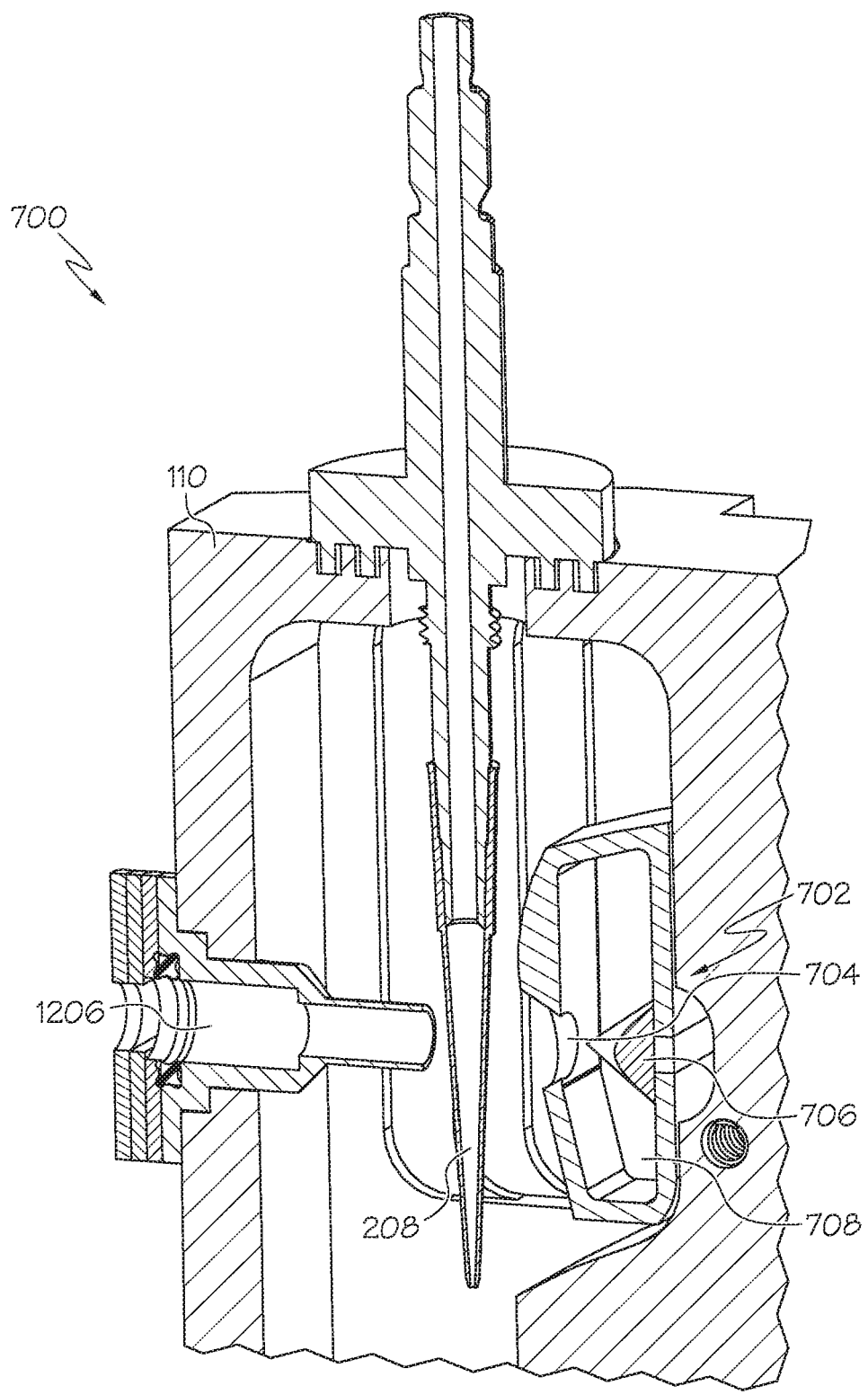
FIG. 7 is a partial section view of the portion of the optical subassembly of FIG. 3 with a pipettor disposed within the optical subassembly.

FIG. 7 illustrates how fluorescence excitation light enters the optics box 110. FIG. 7 shows a partial section view 700 of the optics box 110 with the optics pipettor 108 disposed therein. When the optics pipettor 108 is disposed within the optics box 110, the clear tip 208 may be located within close proximity to the common terminus end 1206 of the bifurcated fiber optic cable 1202. The proximity of the common terminus end 1206 to the clear tip 208 within the optics box 110 may allow the fluorescence excitation light emitted from the common terminus end 1206 to be projected onto a sample located within the clear tip 208. When fluorescence excitation light is projected onto a sample within the clear tip 208, a response reaction may occur within the sample. For instance, the fluo-beads in the clear tip 208 may have a fluorescent label bound to them. The molecules in the label can absorb the excitation light energy which may raise the molecular energy state. The excited states may spontaneously deexcite to produce the fluorescent light that the optical sensor 316 detects.

The portion of the common terminus end 1206 that comes from the transmission end 1208 of the bifurcated fiber optic cable 1202 may capture the response reaction of the sample within the clear tip 208 when the fluorescence excitation light is projected thereon. The visual aspects of the response reaction may be transferred from the common terminus end 1206, through the fiber optic filter housing 1212, and out of the transmission end 1208 where it can be observed by the optical sensor 316. To ensure that the transmission end 1208 is not transferring unwanted reflected fluorescence excitation light at the common terminus end 1206, a light trap 702 may be located behind the clear tip 208 relative to the common terminus end 1206.

The light trap 702 may substantially inhibit any fluorescence excitation light projected from the common terminus end 1206 from being reflected off of the interior surfaces of the optics box 110 and into the first transmission fiber optic bundle 1214 of the common terminus end 1206. The light trap 702 may prevent reflection of the fluorescence excitation light by allowing any residual fluorescence excitation light not absorbed by the sample within the clear tip 208 to enter the light trap 702 through a light trap opening 704. After fluorescence excitation light enters the light trap opening 704, a diverter 706 may disperse the fluorescence excitation light about an interior region 708 of the light trap 702. The diverter 706 and the interior region 708 can be comprised of a substantially non-reflective surface that prevents any light introduced into the light trap 702 from being reflected out of the light trap 702.

Figure 10:
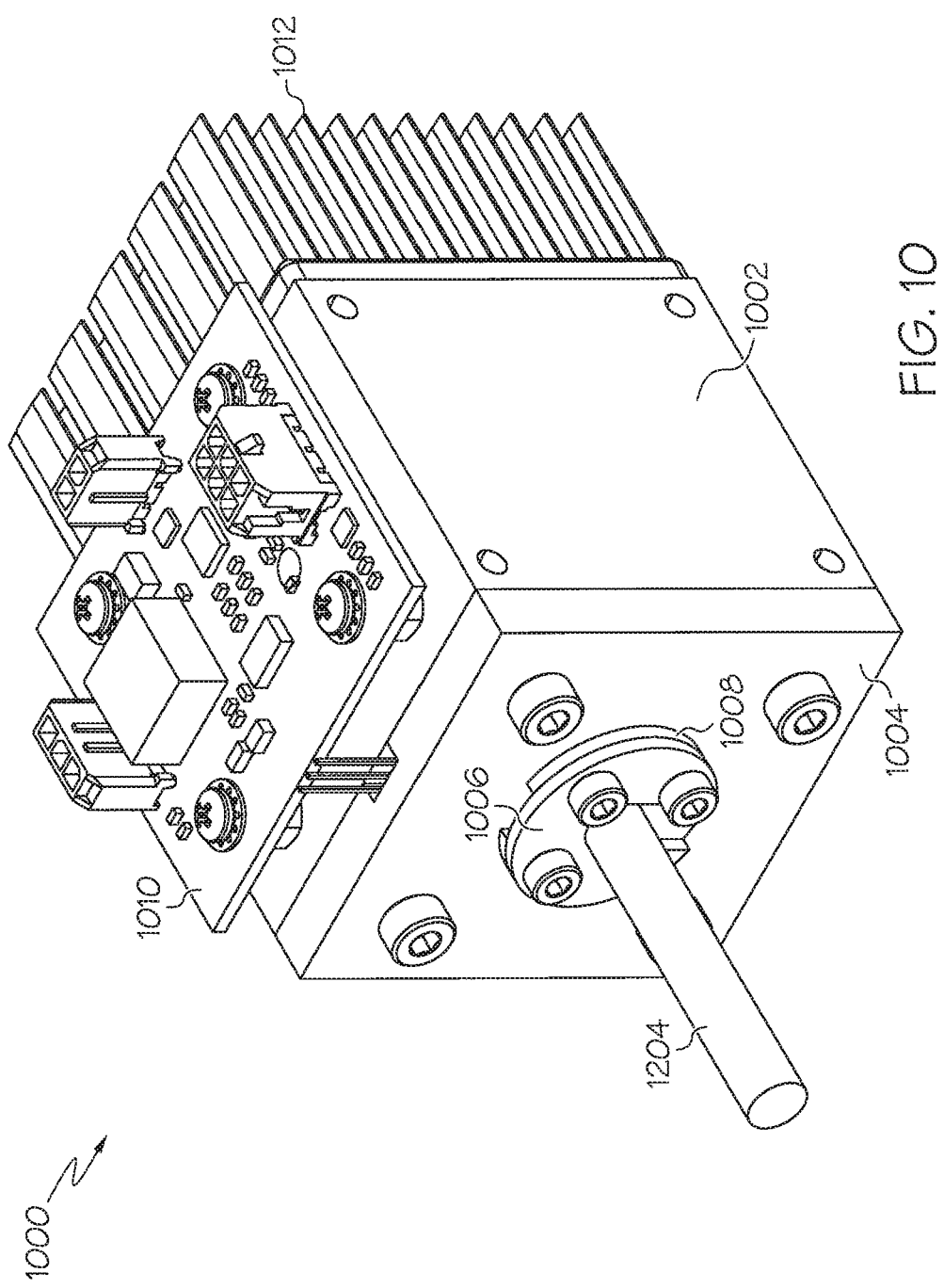
FIG. 10 is a perspective view of a fluorescence excitation subassembly in accordance with the teachings of the present application.
Figure 11:
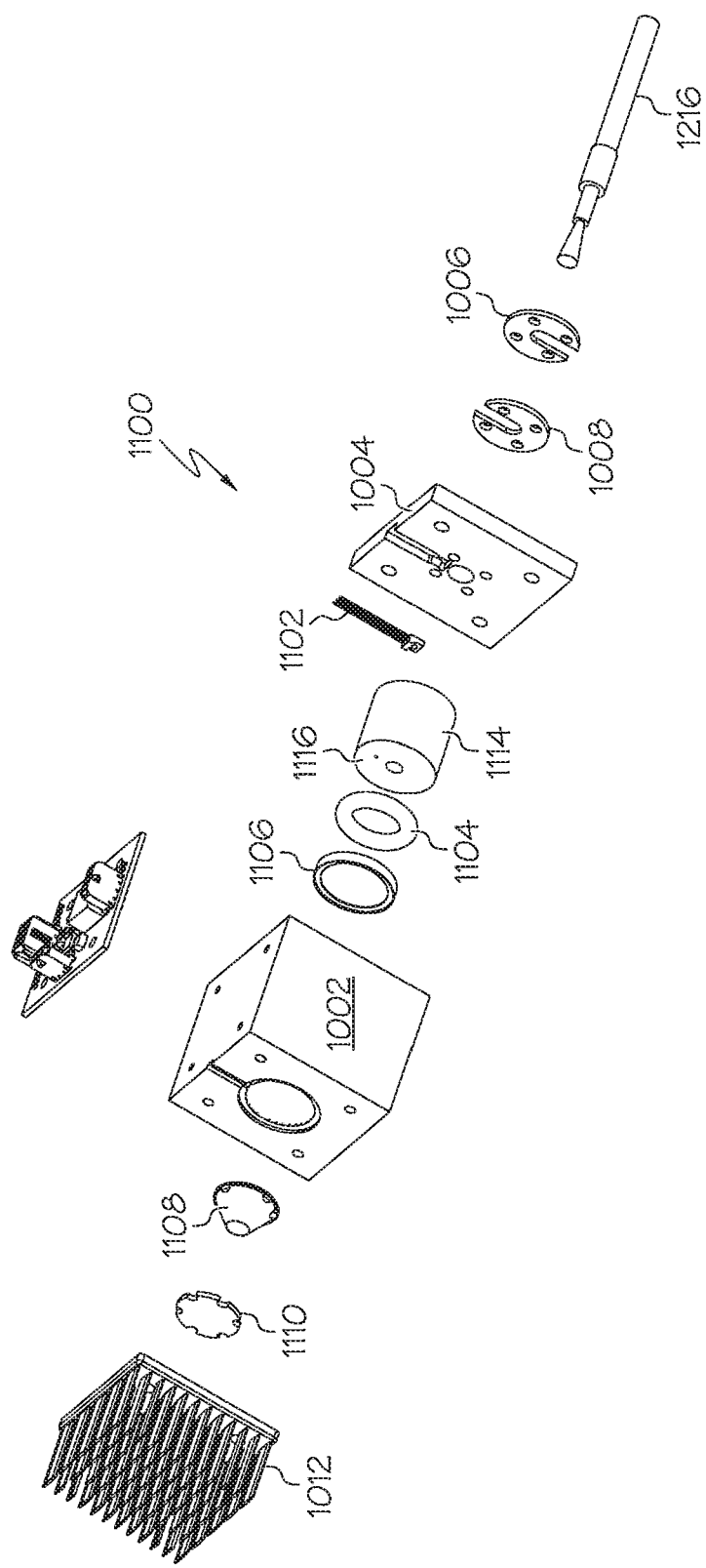
FIG. 11 is a section view of the fluorescence excitation subassembly of FIG. 10.

FIGS. 10 and 11 illustrate the fluorescence excitation source. More particularly, FIG. 10 shows a perspective view of a fluorescence excitation assembly 1000. The fluorescence excitation assembly 1000 is mounted in a separate enclosure from the optics box 110. In accordance with one aspect of the present disclosure, the light source is a high-powered LED with spectral output that will efficiently excite a fluorescent label on paramagnetic particles within a sample, although other light sources, such as lasers or laser diodes can be used as well. A lens, mounted to an LED circuit board, can focus the light onto the end of a fiber optic bundle. Before entering the fiber, the excitation light can pass through a narrow band pass optical filter so that out-of-band light, a potential source of background radiation, can be greatly reduced. The optical fibers in the fiber bundle can have a relatively low numeric aperture in order to greatly reduce the amount of wide angle excitation light that might impinge on the sample and contribute to backgrounds. A silicon photodiode in the excitation light source can be used to monitor the light intensity of the LED. A passive heat sink can be attached to the light source to keep the temperature within its nominal operating range.

In more detail of one embodiment, the fluorescence excitation assembly 1000 may comprise of a body 1002, a first cover 1004, a first fiber optic cover 1006, a second fiber optic cover 1008, a control board 1010, and a heat sink 1012. The fluorescence excitation emission end 1204 of the bifurcated fiber optic cable 1202 may terminate within the body 1002 of the fluorescence excitation assembly 1000. Further, the first and second fiber optic covers 1006, 1008, may couple the fluorescence excitation emission end 1204 of the bifurcated fiber optic cable 1202 to the fluorescence excitation assembly 1000. The first and second fiber optic covers 1006, 1008 may be substantially U-shaped plates that are parallel to one another and oriented 180 degrees to one another. This particular orientation may allow the first and second fiber optic covers 1006, 1008 to couple the bifurcated fiber optic cable 1202 to the fluorescence excitation assembly 1000 without allowing any external light into, or out of, the interior region of the fluorescence excitation assembly 1000.

FIG. 11 shows an expanded view 1100 of the fluorescence excitation assembly 1000. The interior region of the body 1002 may further house a light sensor 1102, an excitation O-ring 1104, an excitation light filter 1106, an excitation lens 1108, and a light-emitting diode (LED) 1110. The LED 1110 may be positioned with one surface substantially contacting the heat sink 1012 and with a light-emitting portion substantially facing the interior region of the body 1002. The LED 1110 may be coupled to the heat sink 1012 with a thermal coupling compound that allows a substantial amount of the heat generated by the LED 1110 to be transferred to the heat sink 1012. The heat sink 1012 can maintain a desired operating temperature of the LED 1110.

The LED 1110 may be oriented to emit light through the excitation lens 1108. The excitation lens 1108 may in turn focus the light emitted by the LED 1110 so that it is substantially directed onto the fluorescence excitation emission end 1204 of the bifurcated fiber optic cable 1202. Before the light emitted by the LED 1110 enters the bifurcated fiber optic cable 1202, it may pass through the excitation light filter 1106. The excitation light filter 1106 may be a fluorescence excitation filter that corresponds with an excitation spectrum of the fluo-bead sample located within the clear tip 208 at the common terminus end 1206. Further, the excitation O-ring 1104 may be positioned within the interior region of the body 1002 between a holder 1114 and the excitation light filter 1106. The O-ring may maintain the correct position of the light filter with respect to the LED 1110 and the emissions fiber optic cable bundle 1216.

The light sensor 1102 may be coupled to the first cover 1004 and oriented to allow the light sensor 1102 to measure the light emissions in the interior region of the fluorescence excitation assembly 1000. The light sensor 1102 may be disposed behind the holder 1114. Further, the holder 1114 may have a light path through hole 1116 that substantially corresponds to the location of the light sensor 1102 and allows the light sensor 1102 to substantially observe the state of the LED 1110. The light sensor 1102 may also be electronically coupled to the control board 1010. The control board 1010 may monitor measurements observed by the light sensor 1102 to determine the fluorescence excitation assembly's 1000 interior conditions. For example, the light sensor 1102 may be utilized by the control board 1010 to determine whether LED 1110 is emitting light. Further, the light sensor 1102 could be used to determine and regulate the intensity of the light emitted by the LED 1110. The control board 1010 can further be in electronic communication with a system control that may control the intensity and timing of the LED 1110.

According to one embodiment in accordance with the present disclosure, the optical system utilizes a bifurcated fiber optic bundle, which includes two fiber optic bundles tied together at a common terminus proximal to the optical sample with one bundle transmitting fluorescence excitation light from a light source to the sample, and with the other bundle receiving fluorescence emission light from the sample at the common terminus and transmitting that light to an optical detector. In another embodiment, the fiber optics may include two separate fiber optic bundles, one to transmit excitation light from source to sample, and the other oriented at an angle, such as, for instance, 90.degree., with respect to the excitation bundle, for receiving the fluorescence emission light and transmitting it to the optical detector.

Figure 8:
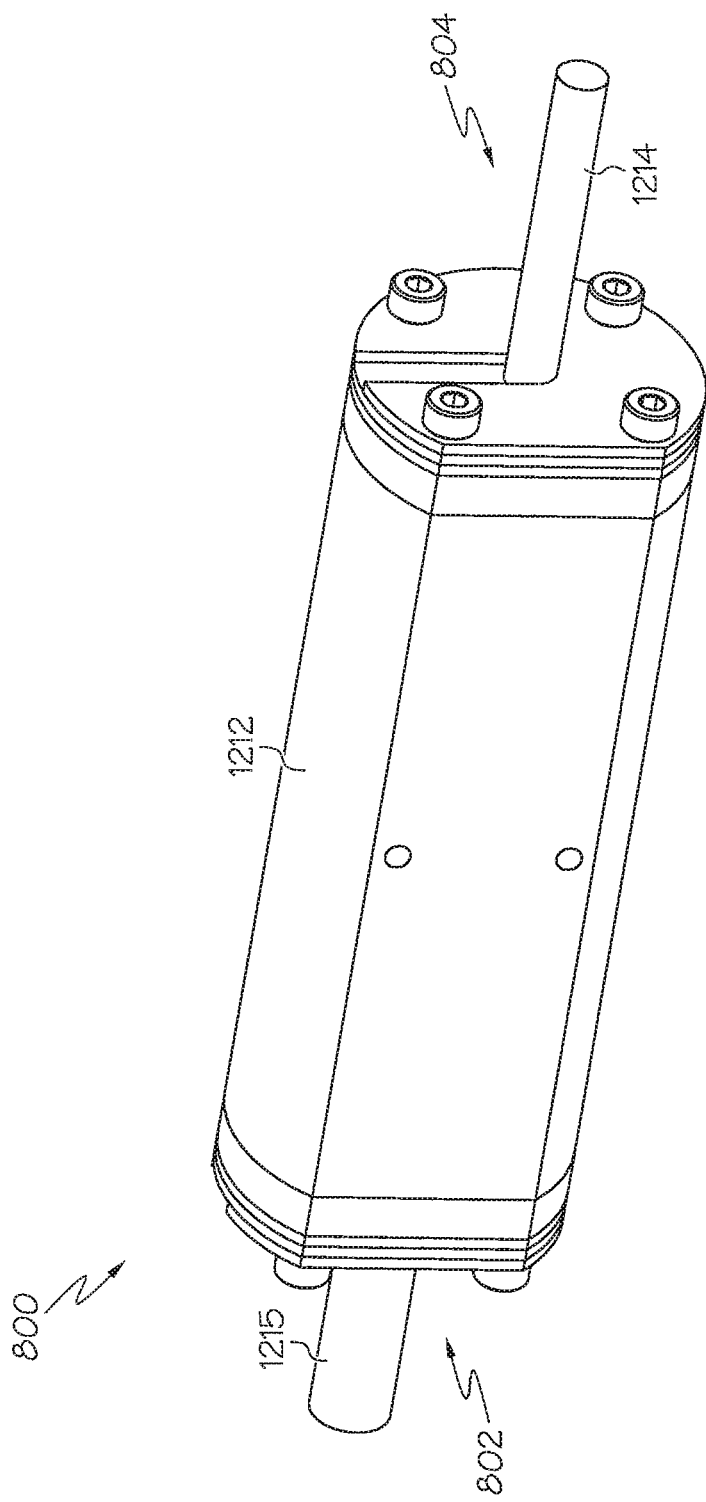
FIG. 8 is a perspective view of an in-line fiber optic light filter assembly in accordance with the teachings of the present application.
Figure 9:
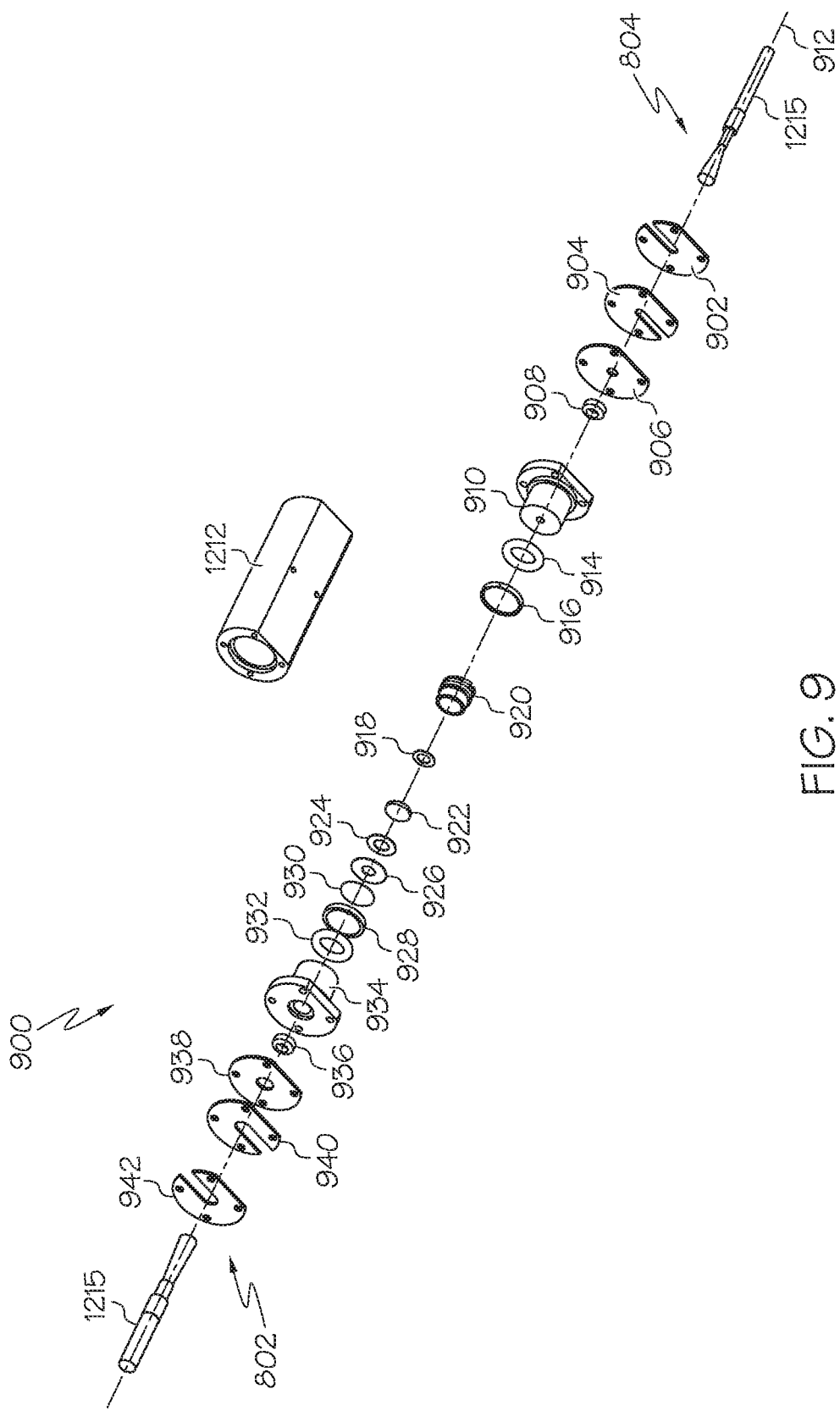
FIG. 9 is an exploded perspective view of the in-line fiber optic light filter assembly of FIG. 8.

The first and second transmission fiber optic cable bundle 1214, 1215 may utilize fiber optic cables to connect the common terminus end 1206 to the transmission end 1208. However, between the common terminus end 1206 and the transmission end 1208 is the fiber optic filter housing 1212. FIGS. 8 and 9 illustrate with more detail the fiber optic filter housing 1212. FIG. 8 specifically shows a perspective view 800 of the fiber optic filter housing 1212 and how the fiber optic filter housing 1212 can be placed in-line with the first and second transmission fiber optic cable bundle 1214, 1215. Further, the fiber optic filter housing 1212 may have an output end 802 and an input end 804. The input end 804 may be an input location where transmissions along the first transmission fiber optic cable bundle 1214 are input into the fiber optic filter housing 1212. Accordingly the output end 802 of the fiber optic filter housing 1212 may be an output location where transmissions are output to the second transmission fiber optic cable bundle 1215.

FIG. 9 is an exploded view 900 of the fiber optic filter housing 1212. The input end 804 illustrates how the first transmission fiber optic cable bundle 1214 can enter the fiber optic filter housing 1212. More particularly, a first entrance plate 902 and a second entrance plate 904 may substantially couple the first transmission fiber optic cable bundle 1214 to the fiber optic filter housing 1212. Both the first and the second entrance plate 902, 904 may be substantially U-shaped and provide a central cavity that is substantially sized to allow the first transmission fiber optic cable bundle 1214 to be disposed therein. Further, the first entrance plate 902 may be parallel to and concentric with the second entrance plate 904 with the U-shaped portions being oriented 180 degrees opposite of one another. The 180 degree orientation of the first and second entrance plate 902, 904 can create a substantially circular through hole through the center of the first and second entrance plates 902, 904 when they are coupled to one another. The through hole may be substantially the same diameter as a cross section of the first transmission fiber optic cable bundle 1214.

After the first and second entrance plate 902, 904, there may be an entrance seal retention plate 906. The entrance seal retention plate 906 may have a through hole that is concentric with the first and second entrance plate 902, 904. Further, the entrance seal retention plate 906 through hole may be substantially the same size as the first and second entrance plate 902, 904 through hole. The entrance seal retention plate 906 through hole may also correspond with an entrance O-ring 908. The entrance O-ring 908 may have a diameter large enough to allow the entrance O-ring 908 to encircle the first transmission fiber optic cable bundle 1214. The entrance O-ring 908 may further become disposed between the entrance seal retention plate 906 and an entrance end cap 910.

The entrance end cap 910 may also have a first partial through hole sufficiently sized to allow the first transmission fiber optic cable bundle 1214 to be substantially disposed therein. The first partial through hole may be sized to terminate at a second partial through hole that may have a slightly smaller diameter than the first partial through hole. The first and second partial through holes of the entrance end cap 910 may allow the first transmission fiber optic cable bundle 1214 to be substantially located within, but not all the way through, the entrance end cap 910. Further, the first transmission fiber optic cable bundle 1214 may fit into the entrance end cap 910 until it contacts the second partial through hole. The slightly smaller diameter of the second partial through hole may ensure that the first transmission fiber optic cable bundle 1214 is correctly positioned within the fiber optic filter housing 1212 while simultaneously allowing the first transmission fiber optic cable bundle 1214 to project a light source through the fiber optic filter housing 1212. To accommodate the entrance O-ring 908, the entrance end cap 910 may also have a recessed portion that allows the entrance O-ring 908 to be at least partially disposed within the recessed portion when the entrance seal retention plate 906 is coupled to the entrance end cap 910.

Regarding the input end 804, the first transmission fiber optic cable bundle 1214 may be disposed within the through hole of the entrance end cap 910. Further, the entrance O-ring 908, the entrance seal retention plate 906, and the first and second entrance plate 902, 904 may be coupled to the entrance end cap 910 with the first transmission fiber optic cable bundle 1214 disposed therein. The entrance O-ring 908 can substantially seal the first transmission fiber optic cable bundle 1214 to the entrance end cap 910. The entrance end cap 910 may further be coupled to the fiber optic filter housing 1212. When the first transmission fiber optic cable bundle 1214 is disposed within the entrance end cap 910, the entrance O-ring 908, the entrance seal retention plate 906, and the first and second entrance plate 902, 904, the first transmission fiber optic cable bundle 1214 may be held in substantially concentric alignment with a central axis 912.

After the entrance end cap 910, a first internal O-ring 914, a first filter 916, a first aperture 918, a lens holder 920, a lens 922, a second aperture 924, a third aperture 926, a second filter 928, a third filter 930 and a second internal O-ring 932 may all be disposed within the fiber optic filter housing 1212. Following the entrance end cap 910, the first internal O-ring 914 can ensure the first filter 916 remains disposed in alignment with the first transmission fiber optic cable bundle 1214. After the first filter 916, the lens holder 920 may hold the first aperture 918. The lens holder 920 may be threaded about its exterior surface that allows the lens holder 920 to be coupled to a corresponding threaded interior surface of the fiber optic filter housing 1212. Further, the lens 922 may be disposed within the fiber optic filter housing 1212 so that it may be seated against an internal retention shelf of the fiber optic filter housing 1212. After the lens 922 is seated against the internal retention shelf, the lens 922 holder may be threadably coupled to the fiber optic filter housing 1212, thereby retaining the lens 922 against the internal retention shelf.

Following the lens 922 and within the fiber optic filter housing 1212 may be the second aperture 924, the third aperture 926, the second filter 928, the third filter 930, and the second internal O-ring 932. The second and third apertures 924, 926 may be substantially circular and contain through holes. The second aperture 924 may have a slightly smaller external diameter than the third aperture 926. Further the fiber optic filter housing 1212 may have corresponding diameter partial through holes that allow the second and the third apertures 924, 926 to be particularly spaced within the fiber optic filter housing 1212 as they are placed within the corresponding partial through hole.

Next may be the second and third filter 928, 930. The second and third filter 928, 930 may be maintained within the fiber optic filter housing 1212 at least partially by the second internal O-ring 932 that may contact an exit cap 934. The exit cap 934 may be located at the output end 802 of the fiber optic filter housing 1212. Similarly to the input end 804, the output end 802 may have an exit O-ring 936 that can seal the second transmission fiber optic cable bundle 1215 at the output end 802. The exit O-ring 936 can seal the second transmission fiber optic cable bundle 1215 by coupling the second transmission fiber optic cable bundle 1215 to the exit cap 934 with an exit seal retention plate 938, and a first and second exit plate 940, 942. The output end 802 can retain the second transmission fiber optic cable bundle 1215 in alignment with the fiber optic filter housing 1212 in substantially the same way as the input end 804. In one embodiment, the three filters 916, 928, and 930 may be a notch filter to remove the excitation light, a long pass filter to eliminate the luminescence signal, and an emission filter to further reduce any out of band or wide angle light from the fluorescence emission signal.

FIG. 12 shows how one embodiment of the present disclosure transmits light from one source to a common terminus via fiber optics, projects that light onto a sample, observes the sample's optical response through fiber optic cables, filters the observed response and transmits the filtered light to an optical reader. More particularly, the LED 1110 can initially produce a fluorescence excitation light. The light may then pass through the excitation lens 1108 where the light is focused for projection onto one terminus end of the emissions fiber optic cable bundle 1216. Prior to entering the terminus end of the emissions fiber optic cable bundle 1216, the excitation light filter 1106 may filter the light produced by the LED 1110 to promote fluorescence excitation. The filtered light may be carried through the emissions fiber optic cable bundle 1216 to the common terminus end 1206 where it may be projected onto a sample located within the clear tip 208. When the fluorescence excitation light is projected onto the sample, the light may react with the sample to emit a visual response.

The visual response of the sample may be captured by the first transmission fiber optic cable bundle 1214 at the common terminus end 1206. The visual response may further travel through the first transmission fiber optic cable bundle 1214 from the common terminus end 1206 to the fiber optic filter housing 1212. At the fiber optic filter housing 1212, the visual response is projected through the first filter 916, which may be a notch filter that can attenuate undesired frequencies from the visual response, and the first aperture 918 onto the lens 922. The lens 922 may further modify the visual response and project the signal through the second and third aperture 924, 926, and through the second and third filter 928, 930. After the visual response has passed through the second and third filter 928, 930, the filtered visual response may be projected onto the output terminus of the second transmission fiber optic cable bundle 1215.

The second transmission fiber optic cable bundle 1215 may then carry the filtered visual response to the transmission end 1208 terminus. The transmission end 1208 terminus may be disposed within close proximity to, and in alignment with, the optical sensor 316 when the optical sensor 316 is in the third reading position 330. The transmission end 1208 of the second transmission fiber optic cable bundle 1215 may than project the readings observed from the sample within the clear tip 208 to the optical sensor 316.

Figure 13:
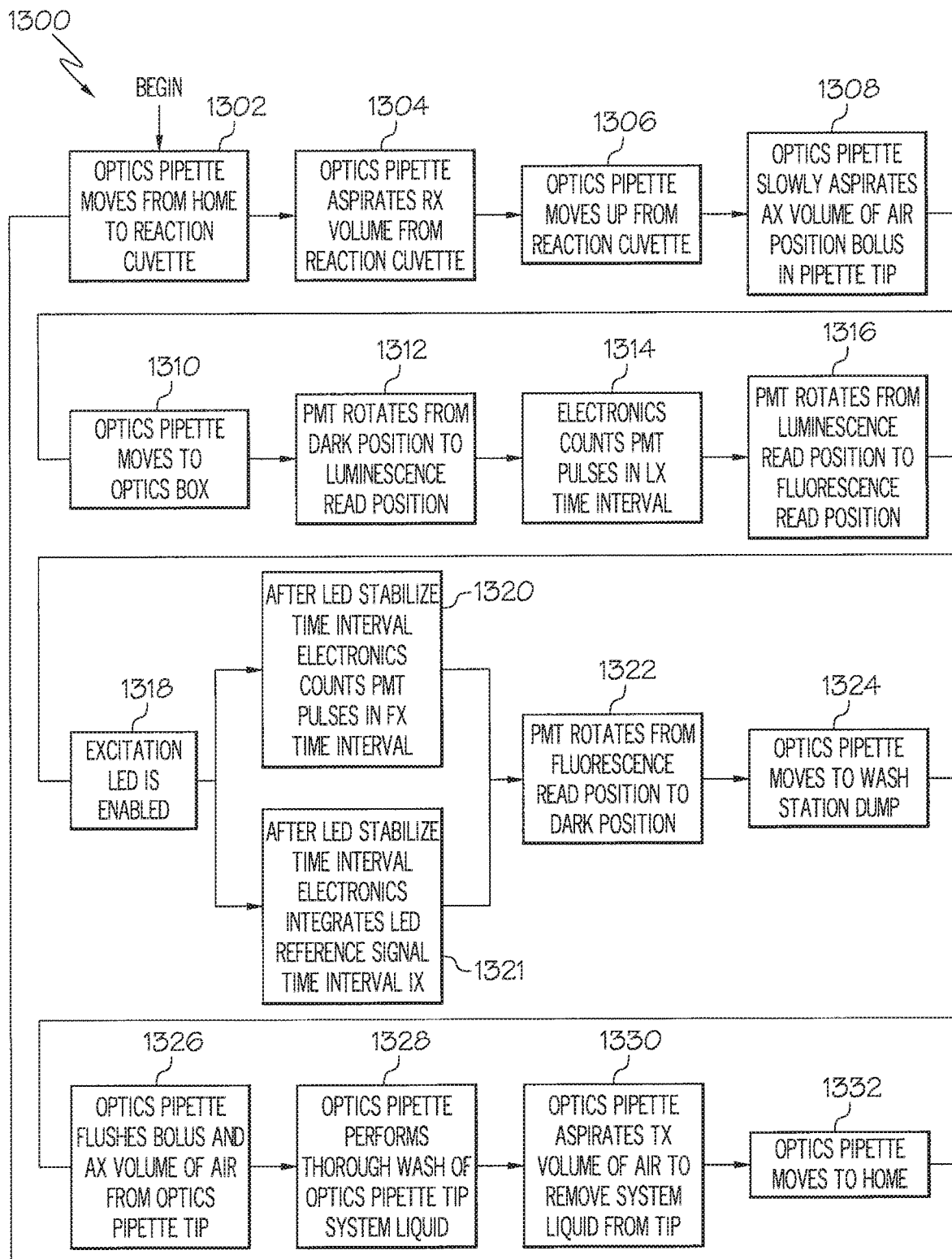
FIG. 13 is a flowchart showing system control logic for the optical subassembly of FIG. 2.

FIG. 13 illustrates how the pipette transfer arm 204, the shutter stepper motor 218, the shutter sensor 318, the optical sensor 316, the LED 1110, and the light sensor 1102 may be electrically coupled too, and controlled by, a system controller 1300. The method of controlling the automated analyzer 100 can initially begin with orienting the pipette transfer arm 204 in a neutral position. From the neutral position, in a first step 1302, the system controller may move the pipette transfer arm 204 to orient the optics pipettor 108 in a position inside a cuvette located in the reaction rotor 106. After the system controller has executed the first step 1302, it may send a command to the optics pipettor 108 to aspirate a volume of a sample from the cuvette in a second step 1304. The system controller may then withdraw the optics pipettor 108 from the cuvette in a third step 1306. While the optics pipettor 108 is located above the cuvette, in a fourth step 1308 the system controller may command the optics pipettor to aspirate a volume of air to position the sample in the clear tip 208. Once the sample is positioned in the clear tip 208, the system controller may move the optics pipettor 108 to a location so that the clear tip 208 is disposed within the optics box 110 in a fifth step 1310.

After the system controller has obtained a sample within the clear tip 208 and positioned the clear tip 208 within the optics box 110, the system controller may send a signal to the shutter stepper motor 218 and the shutter sensor 318 to transition the optical sensor 316 from the second reading position 328 to the first reading position 326 per a sixth step 1312. In a seventh step 1314, the system controller may obtain a luminescence reading from the sample by recording inputs from the optical sensor 316. After obtaining the luminescence reading in the seventh step 1314, the system controller may send a command to the stepper motor 218 and the shutter sensor 318 to transition the optical sensor 316 to the third reading position 330 in an eighth step 1316.

After the optical sensor 316 is oriented to the third reading position 330, the system controller may enable the LED 1110 to emit fluorescence excitation light in a ninth step 1318. The system controller may give the LED 1110 substantial time to stabilize before the system controller will count optical sensor 316 pulses in a time interval 1320. In one embodiment, it may take about 10 milliseconds for the LED 1110 to stabilize and the optical sensor 316 may take readings for 100 milliseconds. Simultaneously with step 1320, in step 1321 the light sensor 1102 may read the LED 1110 reference signal in a time interval. After the system controller has obtained the necessary fluorescence readings from the optical sensor 316 in the tenth step 1320 or the eleventh step 1321, the system controller may execute a twelfth step 1322 where it commands the stepper motor 218 and the shutter sensor 318 to orient the optical sensor 316 in the second position 328.

After the optical sensor 316 is located in the second position 328, in a thirteenth step 1324 the system controller may withdraw the optics pipettor 108 from the optics box 110 and transfer the optics pipettor 108 to the wash station 224. While the optics pipettor 108 is located at the wash station 224, the system controller may send a command to the optics pipettor 108 to flush the sample by dispensing a volume of air during a fourteenth step 1326. After the sample has been flushed from the optics pipettor 108, the system controller may execute a wash cycle during a fifteenth step 1328 where the optics pipettor 108 utilizes a system liquid to wash the optics pipettor 108 clear tip 208. The system controller may execute a final air aspiration in a sixteenth step 1330 to remove any remaining system liquid from the clear tip 208. Finally, the system controller may move the optics pipettor 108 back to a neutral position in anticipation for the next cycle during a seventeenth step 1332.

The system controller can execute the commands shown in FIG. 13 utilizing a plurality of forms known by those skilled in the art. The system controller can execute commands on a time scale with predefined intervals for each command performed by the system controller. The system controller could also utilize the various sensors located throughout the system to determine the appropriate time to move to the next step. For instance, the shutter sensor 318 may communicate to the system controller when the shutter mechanism 314 is in the correct orientation, at which point the system controller may initiate a time sequence prior to transitioning to the next step. One skilled in the art could understand the many ways the system controller could control the automated analyzer 100 such as time sequence commands, proximity sensors, optical sensors, and the like and this disclosure should not be limited to any one embodiment.

While an exemplary embodiment incorporating the principles of the present application has been disclosed hereinabove, the present application is not limited to the disclosed embodiments. Instead, this application is intended to cover any variations, uses, or adaptations of the application using its general principles. Further, this application is intended to cover such departures from the present disclosure as come within known or customary practice in the art to which this present application pertains and which fall within the limits of the appended claims.

The terminology used herein is for the purpose of describing particular illustrative embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

The invention is claimed as follows:

1. An optical reader subassembly comprising:
a pipette having an opaque body and a tip, the pipette configured to aspirate a fluid sample and hold the fluid sample within the tip;
a housing including a reentrant seal and an internal area, the housing configured to receive at least the tip of the pipette through the reentrant seal so that the tip of the pipette is located in a light tight manner within the internal area, the reentrant seal configured to contact the opaque body of the pipette to prevent light entry into the internal area of the housing;
a light source positioned to be in proximity to the tip of the pipette when the tip of the pipette is received by the housing, the light source configured to project light through the tip of the pipette and onto the fluid sample held within the tip; and
an optical sensor configured to take a reading of the fluid sample held within the tip of the pipette without any of the fluid sample being injected from the pipette,
wherein the housing is configured to retain the tip of the pipette in the internal area in the light tight manner as the light source projects the light through the tip of the pipette.

2. The optical reader subassembly of claim 1, which includes a pipette transfer arm configured to transfer the pipette to the housing.

3. The optical reader subassembly of claim 1, wherein the pipette includes a disk feature that mates with the reentrant seal of the housing to prevent stray light from entering the internal area of the housing after the tip of the pipette is received by the housing.

4. The optical reader subassembly of claim 3, wherein the disk feature mates with the reentrant seal of the housing by becoming partially disposed within a portion of the reentrant seal of the housing.

5. The optical reader subassembly of claim 1, wherein the optical sensor is configured to move between at least two of: (i) a first position for taking a luminescence reading of the fluid sample; (ii) a second position for taking a dark current or other background measurement; and (iii) a third position for taking a fluorescence reading of the fluid sample.

6. The optical reader subassembly of claim 5, wherein the pipette remains stationary within the housing while the optical sensor moves between the at least two of the first position, the second position and the third position.

7. The optical reader subassembly of claim 1, wherein the pipette remains stationary within the housing while the optical sensor moves to take the reading of the fluid sample held within the tip of the pipette.

8. The optical reader subassembly of claim 1, wherein the optical sensor is configured to take both a fluorescence reading and a luminescence reading of the fluid sample.

9. The optical reader subassembly of claim 1, which includes a light trap to prevent reflectance of the projected light within the internal area of the housing.

10. An optical subassembly comprising:
a pipette having an opaque body and a tip, the pipette configured to aspirate a fluid sample and hold the fluid sample within the tip;
a pipette transfer arm configured to lower at least the tip of the pipette into a light tight area;
a light source positioned to be in proximity to the tip of the pipette when the tip of the pipette is lowered into the light tight area, the light source configured to project light through the tip of the pipette and onto the fluid sample held within the tip; and
an optical sensor configured to take a reading of the fluid sample held within the tip of the pipette without any of the fluid sample being injected from the pipette,
wherein the pipette transfer arm is configured to hold the tip of the pipette stationary in the light tight area in the light tight manner as the light source projects the light through the tip of the pipette, and
wherein the light tight area is contained within a housing including a reentrant seal that is configured to contact the opaque body of the pipette to prevent light entry into the light tight area.

11. The optical subassembly of claim 10, wherein the pipette transfer arm is configured to seal the light tight area as it lowers the tip of the pipette into the light tight area.

12. The optical subassembly of claim 10, wherein the light source and the optical sensor are located within the housing.

13. The optical subassembly of claim 12, wherein the pipette transfer arm is configured to rotate the pipette towards the housing after the pipette has aspirated the fluid sample into the tip.

14. The optical subassembly of claim 10, wherein the light source is positioned to a horizontal side of the tip of the pipette when the tip of the pipette is positioned within the light tight area.

15. The optical reader subassembly of claim 2, further comprising a controller configured to:
   instruct the pipette transfer arm to lower at least the tip of the pipette through the reentrant seal into the internal area of the housing; and
   instruct the light source to activate causing the light to project through the tip of the pipette while the tip of the pipette is positioned within the internal area of the housing.

16. The optical subassembly of claim 10, further comprising a controller configured to:
   instruct the pipette transfer arm to lower at least the tip of the pipette in to the light tight area; and
   instruct the light source to activate causing the light to project through the tip of the pipette while the tip of the pipette is positioned within the light tight area.

17. The optical reader subassembly of claim 1, wherein the tip is an optically clear tip.

18. The optical subassembly of claim 10, wherein the tip is an optically clear tip.

* * * * *